United States Patent [19]

Hassouna

[11] Patent Number: 5,525,477
[45] Date of Patent: Jun. 11, 1996

[54] METHOD FOR DIAGNOSING BLOOD CLOTTING DISORDERS

[75] Inventor: Houria I. Hassouna, Grosse Pointe, Mich.

[73] Assignee: Board of Trustees operating Michigan State University, East Lansing, Mich.

[21] Appl. No.: 308,948

[22] Filed: Sep. 20, 1994

Related U.S. Application Data

[63] Continuation of Ser. No. 124,835, Sep. 21, 1993, abandoned, which is a continuation of Ser. No. 700,935, May 13, 1991, abandoned, which is a continuation of Ser. No. 379,988, Jul. 14, 1989, abandoned.

[51] Int. Cl.$^6$ .................................. C12Q 1/56; C07K 1/00
[52] U.S. Cl. ........................... 435/13; 436/69; 364/497; 530/381; 530/382; 530/383; 530/384
[58] Field of Search .............................. 435/13; 436/69; 364/497; 530/381, 382, 383, 384

[56] References Cited

U.S. PATENT DOCUMENTS 3,486,981  12/1969  Speck .................................. 436/69 X

FOREIGN PATENT DOCUMENTS 0182929  6/1986  European Pat. Off. ................ 435/13

OTHER PUBLICATIONS

Gradwohl's, *Clinical Laboratory Methods and Diagnosis*, Eighth Edition, Edited by Sonnenwirth et al, vol. 1, Chapters 42–45, pp. 1013–1060, Published by The C. V. Mosby Company, St. Louis, 1980.

Ortho diagnostics, Inc. "A Closer Look at Hemostasis—An Introduction to Coagulation", Published by Ortho Diagnostics, Inc. 1975, pp. 1–51.

*Primary Examiner*—Howard E. Schain
*Assistant Examiner*—Abdel A. Mohamed
*Attorney, Agent, or Firm*—Ian C. McLeod

[57]  ABSTRACT

Assay methods for diagnosing blood clotting disorders are described. The assays use data bases for pooled normal plasma (PNP) and plasma from healthy volunteers, males and females ages 18 to 64 years. Charting on a comparative basis of patient plasma and PNP allows the results to be interpreted by reference to the data base. Simple, rapid, inexpensive and highly sensitive and specific assays devised for diagnosing blood clotting disorders are described.

15 Claims, 25 Drawing Sheets

COAGULATION SCREENING TESTS

| ABNORMAL ACTIVATED PARTIAL THROMBOPLASTIN TIME (APTT) | ABNORMAL PROTHROMBIN TIME (PT) | ABNORMAL THROMBIN CLOTTING TIME (TCT) |
|---|---|---|
| DEFICIENCIES:<br>  FLETCHER FACTOR<br>  HMW-KININOGEN<br>  PREKALLIKREIN<br>  FACTOR XII<br>  FACTOR XI<br>  FACTOR IX<br>  FACTOR VIII | FVII DEFICIENCY | |
| AFIBRINOGENEMIA<br><br>FACTOR V DEFICIENCY<br>FACTOR X DEFICIENCY<br>LUPUS ANTICOAGULANT<br>ORAL ANTICOAGULANT<br>LIVER DISEASE<br>POLYCYTHEMIA<br><br>HEPARIN | AFIBRINOGENEMIA<br>HYPOFIBRINOGENEMIA<br>DYSFIBRINOGENEMIA<br><br>FACTOR V DEFICIENCY<br>FACTOR X DEFICIENCY<br>LUPUS ANTICOAGULANT<br>ORAL ANTICOAGULANT<br>LIVER DISEASE<br>POLYCYTHEMIA | AFIBRINOGENEMIA<br>HYPOFIBRINOGENEMIA<br>DYSFIBRINOGENEMIA<br><br><br><br><br><br><br>HEPARIN |
| CLOTTED BLOOD<br>  (ARTIFACT OR DIC)<br>HEPARIN > 0.4u/ML | CLOTTED BLOOD<br>  (ARTIFACT OR DIC)<br>HEPARIN > 0.4u/ML | CLOTTED BLOOD<br>  (ARTIFACT OR DIC)<br>HEPARIN > 0.4u/ML |

*FIG. 1*

| SCREENING PROCEDURES AND ASSAYS | IDENTIFIES | TEST RESULTS | PATHOGENESIS | CLINICAL MANIFESTATIONS |
|---|---|---|---|---|
| PROTHROMBIN TIME ASSAY (PT)<br><br>NORMAL RANGE: 10.3-12.7 SECONDS | IDENTIFIES: FI, II, V, VII, X<br><br>SELECTIVE FOR FVII DEFICIENCY<br><br>SENSITIVE TO PLASMA LEVEL CHANGES: FI, V, VII | LESS THAN 1% DEFICIENCY<br>FV: 48-50 SEC.<br>FVII: 28-30 SEC.<br>FX: 50-52 SEC.<br>FIBRINOGEN; 6MG/DL 32-35 SEC.<br><br>THERAPUTIC RANGE FOR ANTICOAGULANT THERAPY: 1/1/2 TIMES NORMAL RANGE | NEWBORN INHERITED FACOTR DEFICIENCIES<br><br>AGED PLASMA<br>WARFARIN<br>LIVER DISEASE<br>LUPUS ANTICOAGULANT<br>POLYCYTHEMIA<br>AFIBRINOGENEMIA | BLEEDING: UMBILICAL CORD, UTERINE, SURGERY, CHILDBIRTH, TRAUMA, ETC. |
| COAGULATION | | | | |

FIG. 2-1

| COAGULATION | | | | |
|---|---|---|---|---|
| ACTIVATED PARTIAL THROMBOPLASTIN TIME ASSAY (APTT)<br><br>NORMAL RANGE: 20.5-30-5 SECONDS | IDENTIFIES:<br><br>-FACTORS OF THE CONTACT PHASE: PREKALLIKRIEN HMW-K, FXII<br><br>-FACTORS OF THE INTRINSIC PATHWAY: FXI, IX, VIII<br><br>-FACTORS OF THE COMMON PATHWAY: FI, II, V, X<br><br>SELECTIVE FOR: FACTORS OF THE CONTACT PHASE AND INTRINSIC PATHWAY<br><br>SENSITIVITY- CONFERRED BY ACTIVATING AGENT<br><br>KAOLIN AND SILICA ARE RECOMMENDED<br><br>ELLAGIC ACID AND SOY EXTRACT ARE UNRELIABLE | LESS THAN 1% DEFICIENCY:<br><br>HMW-K: 142-158 SEC.<br><br>PREKALLIKRIEN 80-90 SEC.<br><br>FXII: 280-300 SEC.<br><br>FXI: 138-150 SEC.<br><br>FIX: 78-82 SEC.<br><br>FVIII: 77-80 SEC.<br><br>FX: 144-150 SEC.<br><br>FV: 135-140 SEC.<br><br>HIGH DEGREE OF VARIABILITY WITH HEPARIN THERAPY | INHERITED DEFICIENCIES<br><br><br><br>INHERITED DEFICIENCIES<br><br><br><br>INHERITED DEFICIENCIES<br><br>LUPUS ANTICOAGULANT<br>HEPARIN THERAPY<br>LIVER DISEASE<br>POLYCYTHEMIA<br>AFIBRINOGENEMIA | DECREASED FIBRINOLYTIC ACTIVITY<br><br>INCREASED INCIDENCE OF THROMBOTIC DISEASE<br><br>HEMARTHROSIS AND MUSCLE BLEEDING PSEUDO TUMORS<br><br>JOINT AND MUSCLE BLEEDING |

FIG. 2-2

| SCREENING TEST RESULTS | | | | | | POSSIBLE DISORDERS | CONFIRMATORY SPECIFIC ASSAYS |
|---|---|---|---|---|---|---|---|
| CAPILLARY FRAGILITY TESTS | PLATELET COUNT 150-400 K/MM³ | BLEEDING TIME 3-8 MINS. | PT 10.3-12.7 SEC | APTT 21.5-30.5 SEC | TCT 7-8 SEC | | |
| NEGATIVE | 150-400 K/MM³ | >15 MINS. | NO CLOT | NO CLOT | NO CLOT | AFIBRINO-GENEMIA | CHEMICAL FIBRIN-OGEN THROMBIN CLOTTABLE FIBRINOGEN |
| NEGATIVE | 150-400 K/MM³ | 3-5 MINS. | 11-12.8 SECS. | 21-31 SECS. | 12-14 SECS. | FETAL FIBRINOGEN LIVER METASTASIS HEPATOMA | CHEMICAL ASSAY THROMBIN CLOTT-ABLE FIBRINOGEN |
| NEGATIVE | 150-400 K/MM³ | 3-5 MINS. | 11-12 SECS. | 31-33 SECS. | >60 SECS. | HEPARIN | REACT WITH HEPAORB REAGENT QUANTITATIVE HEPARIN ASSAY |
| NEGATIVE | 150-400 K/MM³ | 3-5 MINS. | 10-11 SECS. | 240-300 SECS. | 7-8 SECS. | FXII DEFICIENCY | FXII ASSAY |
| NEGATIVE | 150-400 K/MM³ | 8-12 MINS. | 48-50 SECS. | 135-140 SECS. | 7-8 SECS. | FV OR FX DEFICIENCY | FV ASSAY FX ASSAY |

FIG. 5-1

| NEGATIVE | 150-400 K/MM³ | 8-10 MINS. | 10-11 SECS. | 78-80 SECS. | 7-8 SECS. | DEFICIENCY OF CONTACT PHASE OR INTRINSIC FACTORS ACQUIRED SPECIFIC INHIBITORS LUPUS-LIKE INHIBITOR | ASSAYS FOR LUPUS LIKE INHIBITOR STUDIES SPECIFIC FACTOR ASSAYS |
|---|---|---|---|---|---|---|---|
| NEGATIVE | 150-400 K/MM³ | 3-8 MINS. | 19-23 SECS. | 31-35 SECS. | 7-8 SECS. | ORAL ANTI-COAGULANTS CEPHALO-SPORINS VIT.K DEFICIENCY | FV ASSAY FIX ASSAY |
| NEGATIVE | 150-400 K/MM³ | 8-10 MINS. | 19-23 SECS. | 42-45 SECS. | 12-14 SECS. | ADVANCED LIVER DIS-EASE CLOTTED SPECIMEN | FV ASSAY REPEAT PT, APTT, TCT ON FRESH PLASMA SAMPLE |
| NEGATIVE | 150-400 K/MM³ | 8-10 MINS. | 14-16 SECS. | 21-31 SECS. | 16-18 SECS. | DYSFIBRINO-GENEMIA DYSPROTEIN-EMIA | CHEMICAL ASSAY THROMBIN CLOTT-ABLE FIBRINOGEN PROTEIN ELECTRO-PHORESIS |
| NEGATIVE | 150-400 K/MM³ | 3-5 MINS. | 26 SECS. | 21-31 SECS. | 7-8 SECS. | FVII DEFICIENCY | FVII ASSAY |

FIG. 5-2

|  |  | MOLECULAR WEIGHT | PLASMA CONCENTRATION | HALF-LIFE |
|---|---|---|---|---|
| COAGULATION FACTORS | PROTHROMBIN | 72,000 | 10 MG/DL | 48-60 HOURS |
| | THROMBIN | 36,000 | — | — |
| | FACTOR V | 300,000 | 3 MG/DL | 12-36 HOURS |
| | FACTOR VII | 45,000-53,000 | 15-50 MG/DL | 5-6.5 HOURS |
| | FACTOR VIII:C | 92,000 AND 80,000 POLYPEPTIDE DOUBLET | 0.5-1 MG/DL | 2.9 DAYS |
| | VW FACTOR | POLYMERS 250,000 | 0.5-1 MG/DL | 6-20 HOURS |
| | FACTOR IX | 57,000 | 0.4 MG/DL | 28-40 HOURS |
| | FACTOR X | 54,000 | 0.8-1 MG/DL | 24-56 HOURS |
| | FACTOR XI | 160,000 | 0.2-0.7 MG/DL | 40-80 HOURS |
| ANTICOAGULANT FACTORS | ATIII | 65,000 | 25 MG/DL | 2.5 DAYS |
| | PROTEIN C | 62,000 | 2.5MG/L+09.MG/L | 6-8 HOURS |
| | HEPARIN COFACTOR II | 66,000 | 6 MG/DL | — |
| FACTORS OF CONTACT PHASE | HMW-K | 120,000 | 7-10 MG/DL | 150 HOURS |
| | PREKALLIKREIN | 85,000 | 5MG/DL | 35 HOURS |
| | XII | 80,000 | 3-4 MG/DL | 50-70 HOURS |
| FIBRINOLYSIS FACTORS | UROKINASE | 55,000 | — | 20 MIN. |
| | T-PA | 68,000 | 0.4 MG/DL | 2-10 MIN. |
| | PLASMINOGEN | 86,000 SINGLE CHAIN GLU-PLASMINOGEN 80,000 SINGLE CHAIN LYS-PLASMINOGEN | 21 MG/DL | 2.2 DAYS |
| | PLASMIN | 85,000 | — | 0.1 SEC. |
| FIBRINOLYSIS INHIBITORS | T-PA INHIBITOR | 67,000 | 0.5 MG/DL | 1 MINUTE |
| | ALPHA-2-PI | 50,000 | 7MG/DL | 2.6 DAYS |

FIG. 8

DIAGNOSIS OF ACUTE THROMBOSIS

| Clinical Manifestation | Clinical Testing | Radiographic Findings | Laboratory Testing | | Identifies |
|---|---|---|---|---|---|
| | | | Serum Enzymes | Hemostasis | |
| Acute Chest Pain | Inconclusive | Positive Diagnostic | Elevated Diagnostic | Irrelevant | Coronary Artery Thrombosis |
| Swelling and Edema of Limbs | Inconclusive | Positive Diagnostic | Negative | Antithrombin III ↓<br>Protein C ↓<br>Fibrinogen (no change)<br>Plasminogen ↓ | Deep Vein Thrombosis |
| Acute Abdomen | Laparatomy | Positive Diagnostic | Negative | Single Thrombotic Episode ↓<br>↓ In Initial Stages<br>of Disease | Mesenteric Thrombosis |
| Respiratory Distress | Inconclusive | Positive Diagnostic | Elevated | Chronic Lowgrade DIC: ↓<br>Diagnostic | Pulmonary Embolism |
| Patches of Hemorrhagic Skin Necrosis Very Ill Patient | Inconclusive | Irrelevant | Elevated | Fibrinogen ↓<br>Platelets ↓<br>Fibrin Split Products ↑<br>Antithrombin III ↓<br>Diagnostic | DIC |

FIG. 9

FACTORS OF THE EXTRINSIC PATHWAY

PATIENT:
SAMPLE FROM:
DATE RECEIVED:
PHYSICIAN:

PATIENT NUMBER:

DATE TESTED:
PHONE NUMBER TO CALL:

| SCREENING TESTS | PATIENT CT/SEC | CONTROL CT/SEC | COMMENTS |
|---|---|---|---|
| PT | | | |
| APTT | | | |
| TCT | | | |

MIXING STUDIES (PT IN SEC)

| GFDP (50uL) | PATIENT(50uL) | CONTROL(50uL) | COMMENTS |
|---|---|---|---|
| FACTOR V | | | |
| FACTOR VII | | | |
| FACTOR X | | | |

REFERENCE RANGE: POOLED NORMAL PLASMA OBTAINED FROM 40 HEALTHY INDIVIDUAL DONORS OF BOTH SEXES, AGES 18 TO 64.
CONTROL: NORMAL DISTRIBUTION OF PT, APTT AND FACTOR LEVELS OBTAINED BY ANALYSIS OF CLOTTING TIMES OF 223 SINGLE DONOR PLASMA FROM INDIVIDUALS OF BOTH SEXES, AGES 18 TO 64.
GFDP - GENETIC FACTOR DEFICIENT PLASMA

DIAGNOSIS:

FIG. 10

FACTORS OF THE INTRINSIC PATHWAY

PATIENT:  
SAMPLE FROM:  
DATE RECEIVED:  
PHYSICIAN:

PATIENT NUMBER:

DATE TESTED:  
PHONE NUMBER TO CALL:

| SCREENING TESTS | PATIENT CT/SEC | CONTROL CT/SEC | COMMENTS |
|---|---|---|---|
| PT | | | |
| APTT | | | |
| TCT | | | |

MIXING STUDIES (APTT IN SEC)

| GFDP (50 UL) | PATIENT (50 UL) | CONTROL (50 UL) | COMMENTS |
|---|---|---|---|
| FACTOR V | | | |
| FACTOR VIII | | | |
| FACTOR IX | | | |
| FACTOR X | | | |
| FACTOR XI | | | |
| FACTOR XII | | | |

REFERENCE RANGE:  
   CONTROL: POOLED NORMAL PLASMA OBTAINED FROM 40 HEALTHY INDIVIDUAL DONORS OF BOTH SEXES, AGES 18 TO 64. NORMAL DISTRIBUTION OF PT, APTT AND FACTOR LEVELS OBTAINED BY ANALYSIS OF CLOTTING TIMES OF 223 SINGLE DONOR PLASMA FROM INDIVIDUALS OF BOTH SEXES, AGES 18 TO 64.  
   GFDP = GENETIC FACTOR DEFICIENT PLASMA  
   DIAGNOSIS:

*FIG. 11*

INHIBITOR STUDIES

PATIENT:                                       PATIENT NUMBER:
SAMPLE FROM:
DATE RECEIVED:                      DATE TESTED:
PHYSICIAN:                          PHONE NUMBER TO CALL:

| SCREENING TESTS | PATIENT CT/SEC | CONTROL CT/SEC | COMMENTS |
|---|---|---|---|
| PT | | | |
| APTT | | | |
| TCT | | | |

PT MIXING STUDIES

| GFDP(50uL) | PATIENT(50uL) | CONTROL(50uL) | COMMENTS |
|---|---|---|---|
| FACTOR V | | | |
| FACTOR VII | | | |
| FACTOR X | | | |
| PNP | | | |

APTT MIXING STUDIES

| FACTOR V | | | |
|---|---|---|---|
| FACTOR VIII | | | |
| FACTOR IX | | | |
| FACTOR X | | | |
| FACTOR XI | | | |
| FACTOR XII | | | |
| PNP | | | |

REFERENCE RANGE:
    CONTROL:    POOLED NORMAL PLASMA OBTAINED FROM 40 HEALTHY
                       INDIVIDUAL DONORS OF BOTH SEXES, AGES 18 TO 64.
                       NORMAL DISTRIBUTION OF PT, APTT AND FACTOR
                       LEVELS OBTAINED BY ANALYSIS OF CLOTTING TIMES
                       OF 223 SINGLE DONOR PLASMA FROM INDIVIDUALS OF
                       BOTH SEXES, AGES 18 TO 64.
                       GFDP = GENETIC FACTOR DEFICIENT PLASMA

DIAGNOSIS:

*FIG. 12*

FACTORS OF THE CONTACT PHASE OF PLASMA ACTIVATION

PATIENT:  
SAMPLE FROM:  
DATE RECEIVED:  
PHYSICIAN:

PATIENT NUMBER:

DATE TESTED:  
PHONE NUMBER TO CALL:

| SCREENING TESTS | PATIENT CT/SEC | CONTROL CT/SEC | COMMENTS |
|---|---|---|---|
| PT | | | |
| APTT | | | |
| TCT | | | |

APTT MIXING STUDIES

| GFDP(50uL) | PATIENT(50uL) | CONTROL(50uL) | COMMENTS |
|---|---|---|---|
| FACTOR XI | | | |
| FACTOR XII | | | |
| FL.F | | | |
| HMWK | | | |

FL.F = FLETCHER FACTOR(PREKALLIKEIN)  
HMWK = HIGH MOLECULAR WEIGHT KININOGEN

REFERENCE RANGE:  
    CONTROL:    POOLED NORMAL PLASMA OBTAINED FROM 40 HEALTHY INDIVIDUAL DONORS OF BOTH SEXES, AGES 18 TO 64. NORMAL DISTRIBUTION OF PT, APTT AND FACTOR LEVELS OBTAINED BY ANALYSIS OF CLOTTING TIMES OF 223 SINGLE DONOR PLASMA FROM INDIVIDUALS OF BOTH SEXES, AGES 18 TO 64.  
    GFDP = GENETIC FACTOR DEFICIENT PLASMA

DIAGNOSIS:

*FIG. 13*

ANTI-THROMBIN III ASSAYS

PATIENT:  
SAMPLE FROM:  
DATE RECEIVED:  
PHYSICIAN:

PATIENT NUMBER:

DATE TESTED:  
PHONE NUMBER TO CALL:

| SCREENING TESTS | PATIENT CT/SEC | CONTROL CT/SEC | COMMENTS |
|---|---|---|---|
| PT | | | |
| APTT | | | |
| TCT | | | |

| | | | |
|---|---|---|---|
| TCT (DEFIBRINATED PLASMA 100uL) | | | |
| TCT + HEPARIN | | | |
| TROMBIN INACTIVATED (u/ML) | | | |
| % ANITHROMBIN III/HEPARIN COFACTOR ACTIVITY | | | |
| IMMUNOREACTIVE LEVELS ATIII | | | |
| PROGRESSIVE ACTIVITY ATIII | | | |

NORMAL RANGE = 70 TO 100% PATIENT ATIII ACTIVITY:

REFERENCE RANGE:  
    CONTROL:    POOLED NORMAL PLASMA OBTAINED FROM 40 HEALTHY INDIVIDUAL DONORS OF BOTH SEXES, AGES 18 TO 64. NORMAL DISTRIBUTION OF PT, APTT AND FACTOR LEVELS OBTAINED BY ANALYSIS OF CLOTTING TIMES OF 223 SINGLE DONOR PLASMA FROM INDIVIDUALS OF BOTH SEXES, AGES 18 TO 64.  
    GFDP = GENETIC FACTOR DEFICIENT PLASMA

DIAGNOSIS:

*FIG. 14*

PROTEIN C ASSAY

PATIENT:  
SAMPLE FROM:  
DATE RECEIVED:  
PHYSICIAN:

PATIENT NUMBER:

DATE TESTED:  
PHONE NUMBER TO CALL:

| SCREENING TESTS | PATIENT CT/SEC | CONTROL CT/SEC | COMMENTS |
|---|---|---|---|
| PT | | | |
| APTT | | | |
| TCT | | | |

PATIENT

| ASSAY: | BEFORE ACTIVATION | TTP | SNAKE VENOM | Δ ACTIVITY (FOLD DIFFERENCE) |
|---|---|---|---|---|
| FV CT/SEC. | | | | |
| FVIII CT/SEC. | | | | |
| ACTIVITY % | | | | |

PERCENT PROTEIN C ACTIVITY:  
NORMAL RANGE: 60 TO 100%

PERCENT PROTEIN S ACTIVITY:  
NORMAL RANGE: 60 TO 100%

REFERENCE RANGE:  
    CONTROL: POOLED NORMAL PLASMA OBTAINED FROM 40 HEALTHY INDIVIDUAL DONORS OF BOTH SEXES, AGES 18 TO 64. NORMAL DISTRIBUTION OF PT, APTT AND FACTOR LEVELS OBTAINED BY ANALYSIS OF CLOTTING TIMES OF 223 SINGLE DONOR PLASMA FROM INDIVIDUAL DONORS OF BOTH SEXES, AGES 18 TO 64.

DIAGNOSIS:

*FIG. 15*

FIBRINOGEN ASSAY

PATIENT:                                       PATIENT NUMBER:
SAMPLE FROM:
DATE RECEIVED:                       DATE TESTED:
PHYSICIAN:                           PHONE NUMBER TO CALL:

| SCREENING TESTS | PATIENT CT/SEC | CONTROL CT/SEC | COMMENTS |
|---|---|---|---|
| PT | | | |
| APTT | | | |
| TCT | | | |

| THROMBIN CLOTTING TIME (TCT) | PATIENT | | PNP | |
|---|---|---|---|---|
| PLASMA DILUTIONS | CT/SEC | OGEN MG/DL | CT/SEC | OGEN MG/DL |
| 1   100.00 UL | | | | 200.00 |
| 2   50.00 UL | | | | 100.00 |
| 3   25.00 UL | | | | 50.00 |
| 4   12.50 UL | | | | 25.00 |
| 5   6.25 UL | | | | 12.25 |
| 6   3.12 | | | | 6.25 |

NORMAL RANGE: 200 TO 400 MG/DL
PATIENT FIBRINOGEN PLASMA LEVEL:

REFERENCE RANGE:
   CONTROL:     POOLED NORMAL PLASMA OBTAINED FROM 40 HEALTHY
                     INDIVIDUAL DONORS OF BOTH SEXES, AGES 18 TO 64.
                     NORMAL DISTRIBUTION OF PT, APTT AND FACTOR
                     LEVELS OBTAINED BY ANALYSIS OF CLOTTING TIMES
                     OF 223 SINGLE DONOR PLASMA FROM INDIVIDUALS OF
                     BOTH SEXES, AGES 18 TO 64.
                 GFDP = GENETIC FACTOR DEFICIENT PLASMA
DIAGNOSIS:

*FIG. 16*

PATIENT REPORT
BLEEDING WORKUP

PATIENT:
SAMPLE FROM:
DATE RECEIVED:
PHYSICIAN:

PATIENT NUMBER:

DATE TESTED:
PHONE NUMBER TO CALL:

| SCREENING TESTS | PATIENT CT/SEC | CONTROL CT/SEC | COMMENTS |
|---|---|---|---|
| PT | | | |
| APTT | | | |
| TCT | | | |

| | | | |
|---|---|---|---|
| FIBRINOGEN | | | |
| FACTOR V | | | |
| FACOTR VII | | | |
| FACTOR VIII | | | |
| FACTOR IX | | | |
| FACTOR X | | | |
| FACTOR XI | | | |
| LUPUS ANTICOAGULANT | | | |
| IMMUNOREACTIVE LEVELS OF VWF | | | |
| RISTOCETIN COFACTOR ASSAY | | | |

REFERENCE RANGE:
    CONTROL: POOLED NORMAL PLASMA OBTAINED FROM 40 HEALTHY INDIVIDUAL DONORS OF BOTH SEXES, AGES 18 TO 64. NORMAL DISTRIBUTION OF PT, APTT AND FACTOR LEVELS OBTAINED BY ANALYSIS OF CLOTTING TIMES OF 223 SINGLE DONOR PLASMA FROM INDIVIDUALS OF BOTH SEXES, AGES 18 TO 64.
    GFDP = GENETIC FACTOR DEFICIENT PLASMA

DIAGNOSIS:

*FIG. 17*

PATIENT REPORT
HYPERCOAGULABLE WORKUP

PATIENT:  PATIENT NUMBER:
SAMPLE FROM:
DATE RECEIVED:  DATE TESTED:
PHYSICIAN:  PHONE NUMBER TO CALL:

| SCREENING TESTS | PATIENT CT/SEC | CONTROL CT/SEC | COMMENTS |
|---|---|---|---|
| PT | | | |
| APTT | | | |
| TCT | | | |

| | | | |
|---|---|---|---|
| ANTITHROMBIN III | | | |
| PROTEIN C | | | |
| PROTEIN S | | | |
| PLASMINOGEN | | | |
| INHIBITORS TO PA | | | |
| FIBRINOGEN | | | |
| LUPUS INHIBITOR | | | |
| FACTOR XII | | | |
| FLETCHER FACTOR | | | |
| HMW- KININOGEN | | | |

REFERENCE RANGE:
CONTROL: POOLED NORMAL PLASMA OBTAINED FROM 40 HEALTHY INDIVIDUAL DONORS OF BOTH SEXES, AGES 18 TO 64. NORMAL DISTRIBUTION OF PT, APTT AND FACTOR LEVELS OBTAINED BY ANALYSIS OF CLOTTING TIMES OF 223 SINGLE DONOR PLASMA FROM INDIVIDUALS OF BOTH SEXES, AGES 18 TO 64.
GFDP = GENETIC FACTOR DEFICIENT PLASMA

DIAGNOSIS:

*FIG. 18*

| Thrombin Activity | | | Measurement of Plasma ATIII/Heparin Cofactor Activity | | | |
|---|---|---|---|---|---|---|
| Thrombin Inhibited (Units) | Clotting Time (Sec.) | Thrombin Moles | ATIII Moles | ATIII µg/100µL | Percent ATIII Activity/100uL | |
| 1.5 | 7.5 | $1 \times 10^{-11}$ | $1 \times 10^{-11}$ | 0.7 | 0 | |
| 1 | 12 | $0.7 \times 10^{-11}$ | $0.7 \times 10^{-11}$ | 0.49 | 30 | |
| 0.9 to 0.8 | 14 to 16 | $6.3 \times 10^{-12}$ $5.6 \times 10^{-12}$ | $6.3 \times 10^{-12}$ $5.6 \times 10^{-12}$ | 0.42 to 0.37 | 40 to 47 | |
| 0.7 to 0.6 | 18 to 20 | $4.9 \times 10^{-12}$ $4.2 \times 10^{-12}$ | $4.9 \times 10^{-12}$ $4.2 \times 10^{-12}$ | 0.32 to 0.25 | 54 to 65 | |
| 0.5 to 0.4 | 22 to 24 | $3.5 \times 10^{-12}$ $2.8 \times 10^{-12}$ | $3.5 \times 10^{-12}$ $2.8 \times 10^{-12}$ | 0.21 to 0.18 | 70 to 74 | |
| 0.3 to 0.2 | 27 to 28 | $2.1 \times 10^{-12}$ $1.4 \times 10^{-12}$ | $2.1 \times 10^{-12}$ $1.4 \times 10^{-12}$ | 0.14 to 0.09 | 80 to 87 | |
| 0.1 to 0.01 | 30 to 32 | $0.7 \times 10^{-12}$ $0.7 \times 10^{-13}$ | $0.7 \times 10^{-12}$ $0.7 \times 10^{-13}$ | 0.04 to 0.004 | 94 to 100 | |

FIG. 22

| % Factor Activity | FV | FVIII | FIX | FX | FXI |
|---|---|---|---|---|---|
| | | (Clotting Time in Seconds) | | | |
| 40 | 30.38 | 28.97 | 30.12 | 31.53 | 33.80 |
| 35 | 31.73 | 30.16 | 30.61 | 32.18 | 34.77 |
| 30 | 33.08 | 31.35 | 31.10 | 32.83 | 35.73 |
| 25 | 34.43 | 32.54 | 31.58 | 33.48 | 36.68 |
| 20 | 35.78 | 33.73 | 32.06 | | 37.63 |
| 16 | 36.86 | 34.69 | | | |
| 16 | 37.1 | 33.74 | 33.56 | 36.34 | |
| 12 | 42.4 | 37.97 | 35.93 | 39.13 | |
| 8 | 47.7 | 42.20 | 38.30 | 41.91 | 44.59 |
| 4 | 53.0 | 46.42 | 40.67 | 44.70 | 53.29 |
| 2 | | 48.54 | | | 57.65 |
| 2 | 65.75 | 47.54 | 45.11 | 47.42 | 70.95 |
| 1.5 | 77.44 | 55.61 | 47.76 | 52.32 | |
| 1 | 89.14 | 63.68 | 50.40 | 57.23 | 88.51 |
| 0.5 | 100.84 | 71.75 | 53.04 | 62.13 | 97.29 |
| 0 | 112.54 | 79.82 | 78.54 | 67.03 | |

FIG. 29

METHOD FOR DIAGNOSING BLOOD CLOTTING DISORDERS

This is a continuation of application Ser. No. 08/124,835 filed on Sep. 21, 1993, now abandoned, which is a continuation of Ser. No. 07/700,935, filed May 13, 1991, now abandoned, which is a continuation of Ser. No. 07/379,988, filed Jul. 14, 1989, abandoned.

BACKGROUND OF THE INVENTION

(1) Field of the Invention

The present invention relates to an improved method for diagnosing blood clotting disorders based upon clotting times for a plasma from a patient. In particular, the present invention relates to a method which uses a combination of charts, pooled normal plasma (PNP) as a control and data bases for normal and abnormal clotting in the presence of various clotting or clot inhibiting agents in diagnosing a specific clotting disorder.

(2) Prior Art

In the United States about 1.5 million people per year have a heart attack. About half survive, and most require thrombolytic (clot-dissolving) treatments like tPA and streptokinase. About 500,000 people are hospitalized each year in the U.S. because of pulmonary embolism (clot in blood vessels in the lungs) or deep venous thrombosis (clot in vessels of limbs, often in the legs). About 220,000 people per year have coronary by-pass surgery for treatment of heart disease resulting from clots blocking coronary blood vessels. 50,000 people die each year of pulmonary embolism. 200,000 people die each year of cerebrovascular disease. 50,000 persons in the U.S. population have inherited clotting defects.

Diseases caused by blood clots are among the most common life-threatening medical problems in the United States. Another group of important diseases is caused by failure of blood to clot (e.g. hemophilia); a lot of these are inherited defects, but some are caused by other conditions like cancer, Lupus, or even certain infections that affect the liver and other tissues involved in the production of blood proteins. Clotting diseases are on the increase because they are associated with life style patterns in the western world (obesity, lack of exercise, smoking), and with aging. People are living longer these days and therefore more are entering the high risk age groups. A lot more people are consequently put on oral anticoagulants to counter this trend. New types of treatment are now being developed that make it all the more important to be able to reach decisions quickly on which treatment to use and whether or not it is working properly.

Accurate and rapid diagnosis of diseases caused by clots or clotting defects is therefore a major everyday problem for doctors and medical technologists. Consequently, there is a significant segment of the clinical diagnostic industry dedicated to providing products to meet this demand.

Laboratory diagnosis depends on tests done by technicians to measure how long the patient's blood plasma takes to clot, as compared to normal, and then to find out exactly what is wrong when the plasma does not clot properly. To do this, laboratories buy test kits and diagnostic reagents that are designed to help identify the clotting problem or defect. Some tests are simple; others are complex, need expensive equipment and skilled personnel, and take a lot of technician's time. Other tests are so complicated or so costly in reagents that routine laboratories in hospitals and clinics don't even do them, so they send the blood sample away to a specialty laboratory where the tests are performed by experts for a fee.

Several companies in the medical diagnostic field sell coagulation diagnostic kits. However, these kits are mostly based on technological principles developed in the 1950's and the procedures are frequently seriously flawed. Modernization in technique has come primarily in the form of automation by computer-controlled instruments (coagulometers) that provide increased accuracy and avoid human errors, and reduce technician time, but the test principles are still the same. These new instruments are expensive, particularly in their most automatic form. They handle multiple samples and have built-in micro-processors that perform all the computations of results and comparisons to normal values. For some of the tests needed for monitoring clot dissolving treatments (e.g. urokinase, tPA), additional equipment is needed.

The trend in the industry toward automation has come about due to the high cost of technical time, and the demand for more, faster and better diagnostic testing. As pharmaceutical companies develop totally new drugs the need for more tests, performed more frequently and giving more accurate information to the doctor, will increase substantially. Clot-dissolving products are expected to be among the biggest growth areas in the medical therapy market over the next decade. For example, based on sale after FDA approval, tPA is the most successful new drug ever introduced in the United States. The diagnostic industry is going to have to move in the direction of speedier tests, performed as close as possible to the patient and his or her physician. The needs for certain kinds of tests that monitor, for example, tPA infusion therapy or oral anticoagulant prophylaxis will increase. The same is true for the "replacement" treatments that are now appearing for genetic and acquired clotting defects; these new therapies have only become possible because of genetic engineering technology. There are no satisfactory systematic diagnostic approaches available in the marketplace to meet these needs at the moment. There is a need for such a systematic approach.

The prior art procedures employed in most cases are flawed; they are outdated and have not been optimized to meet the level of critical, quantitative diagnostic need in today's clinical setting. Reagents of uncertain value or giving unreliable results are used on the basis of tradition rather than on the basis of rigorous scientific evaluation. Consequently, it is not possible to reach a correct and accurate diagnosis using many of them, and they do not match up to expectations of the clinician for therapeutic monitoring. The more complex tests available today for monitoring need equipment and skills that are not routinely available, and therefore they are only done in reference lab settings; although the clinician needs these kinds of test results, the procedures are not run often enough to provide the best results. In some cases the current diagnostic reagents are not stable and their shelf lives are not well characterized for today's quantitative tests. The variables that influence the test results, like disease state and therapeutic history, have not been examined sufficiently in most cases to permit these kits and reagents to be used with confidence for quantitative purposes. Quantitative test data is needed when powerful therapies are being applied that can be disastrous in the wrong situation.

The complications faced by the clinician in dealing with these new surgical and medical interventions becoming available for patients, coupled with the complexity of the lab technology, have resulted in a serious communication gap between the two. There is a need for a comprehensive approach to differential diagnostic logic in thrombotic and clotting diseases, in a modern form that makes the system available and understandable to both clinical and laboratory personnel.

OBJECTS

It is an object of the present invention to provide tests which have characterized reagents, improved configuration of the assays, quantitative reliability in a wide variety of disease states, and proven interrelationships of test results with clinical and pathological data. Further it is an object to provide tests which are relatively simple and economical. These and other objects will become increasingly apparent by reference to the following description and the drawings.

IN THE DRAWINGS

FIG. 1 is a Table showing the results of testing for prothrombin (P), activated partial thromboplastin (APT) and thrombin (T) in identifying various blood coagulation deficiencies according to the present invention.

FIG. 2 shows the various times corresponding to various blood coagulation deficiencies according to the present invention.

FIG. 5 is a Table showing the clotting times of various assays and the diagnosis.

Figure 3:
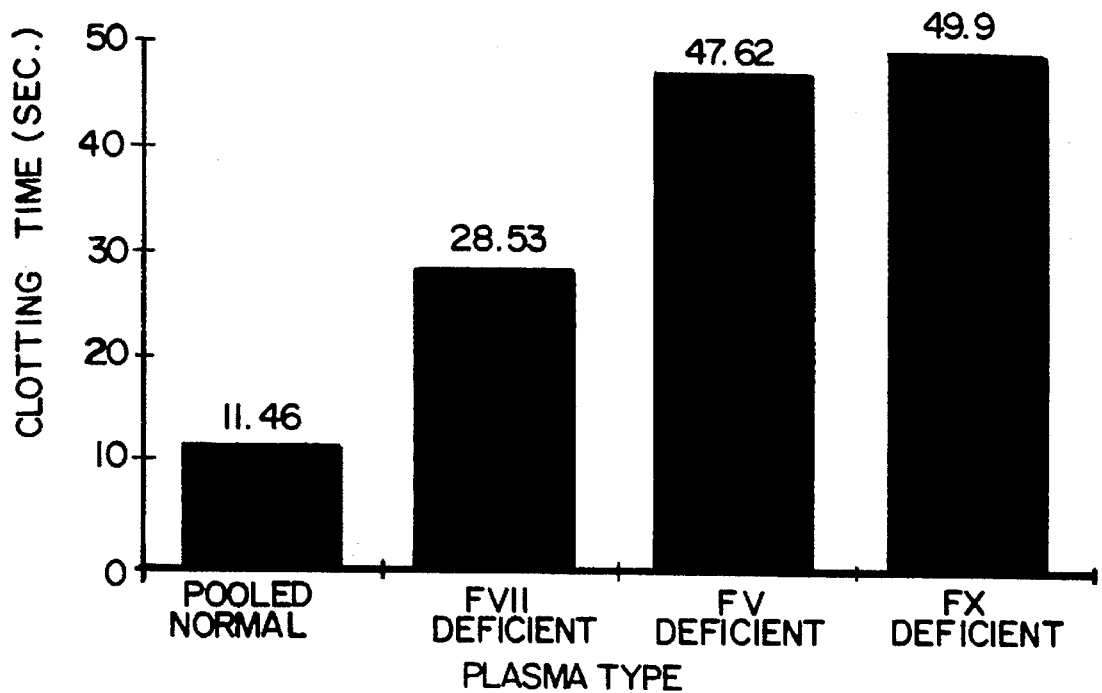
FIG. 3 shows the mean of the clotting time of pooled normal plasma (PNP) and Factors V, VII and X genetically deficient plasma (less than 1% Factor activity) which is measured by the P assay.
Figure 6:
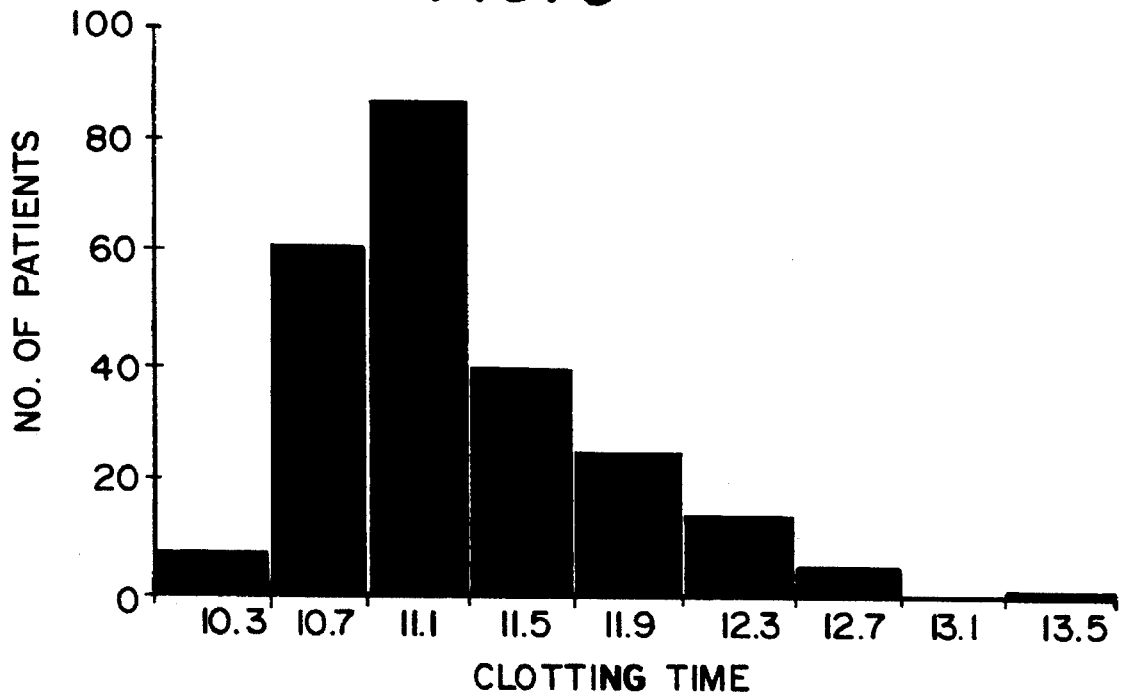
Figure 4:
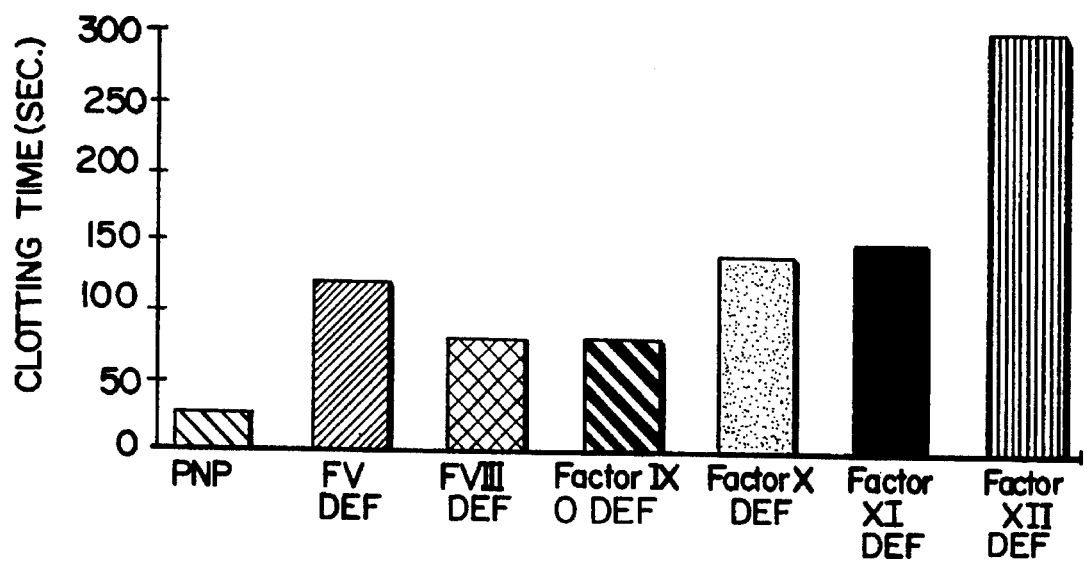
FIG. 4 shows the comparative clotting time by the APTT assay for zero percent Factor activity as indicated.

FIG. 6 shows the normal range of the mean clotting time of 233 individuals, ages 18 to 64, using citrated human plasma samples measured by the P time assay. The mean is 11.4 and the median is 11.3. The range is 10.3 to 12.7. PNP (100 ul) was clotted with reconstituted 200 ul tissue thromboplastin/calcium chloride (TTP/CaCl$_2$ powder, Ortho Diagnostic Systems, Raritan, N.J.) to give a clotting time of 11.6±0.5 seconds with PNP.

Figure 7:
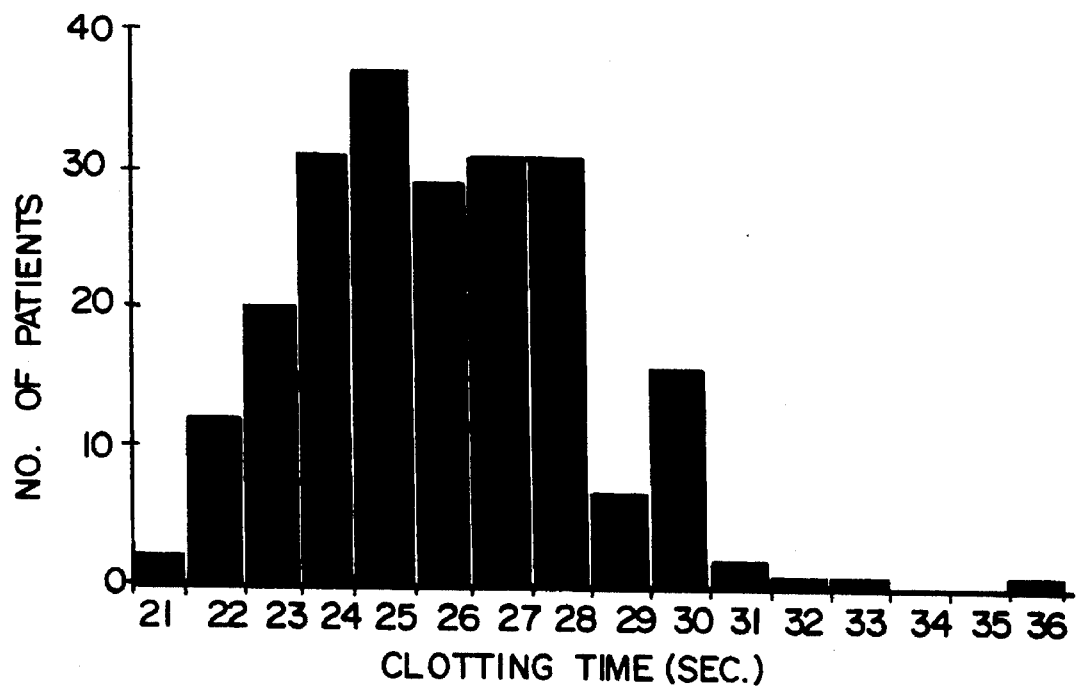

FIG. 7 shows the normal range of the mean clotting time of 221 individuals using citrated human plasma samples measured by the APT time assay. The mean is 26.6 and the median is 23.5.

FIG. 8 is a chart characterizing the various factors in blood plasma.

FIG. 9 is a table showing the various tests which are used to finally diagnose a thrombosis disease. The hemostasis assays of the present invention are shown in the context of this diagnosis.

FIG. 10 is a chart which is used for recording the assays for factors of the entrinsic pathway.

FIG. 11 is a chart which is used for recording assays for the factors of the intrinsic pathway.

FIG. 12 is a chart which is used for recording assays for inhibitors.

FIG. 13 is a chart which is used for recording the assays of the factors of the contact phase of plasma activation.

FIG. 14 is a chart which is used for recording the assays of the antithrombin III assays.

FIG. 15 is a chart which is used for recording the assay for protein C.

FIG. 16 is the chart used for recording the assay for fibrinogen.

FIG. 17 is a chart which is used for recording a bleeding workup.

FIG. 18 is a chart which is used for recording a hypercoagulation workup.

Figure 19:
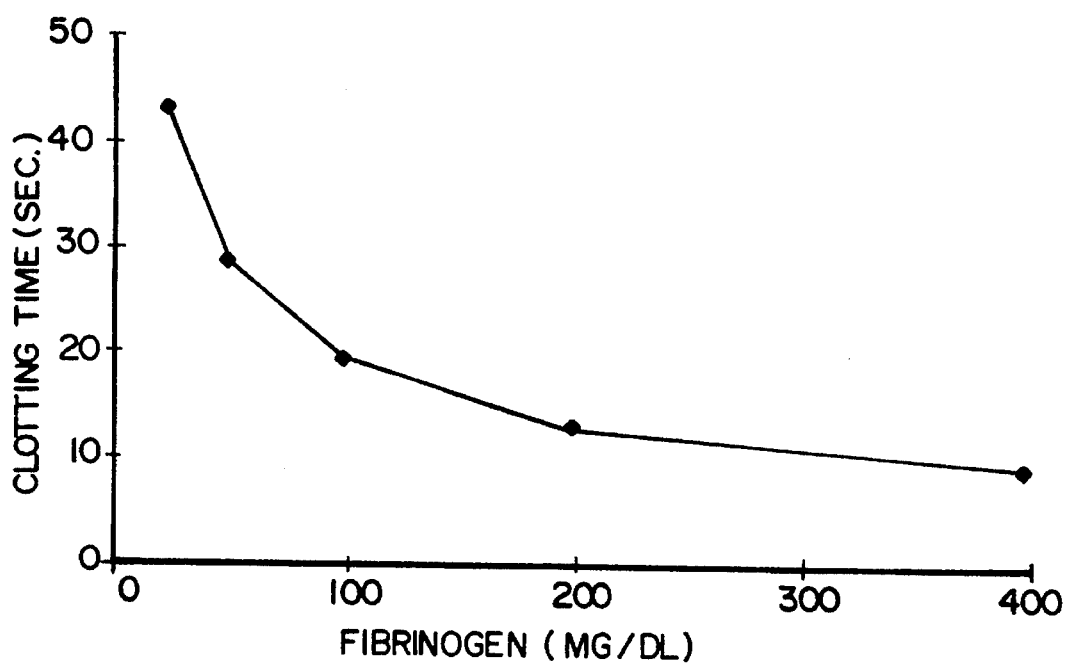

FIG. 19 is a graph showing fibrinogen concentration versus clotting time.

Figure 20:
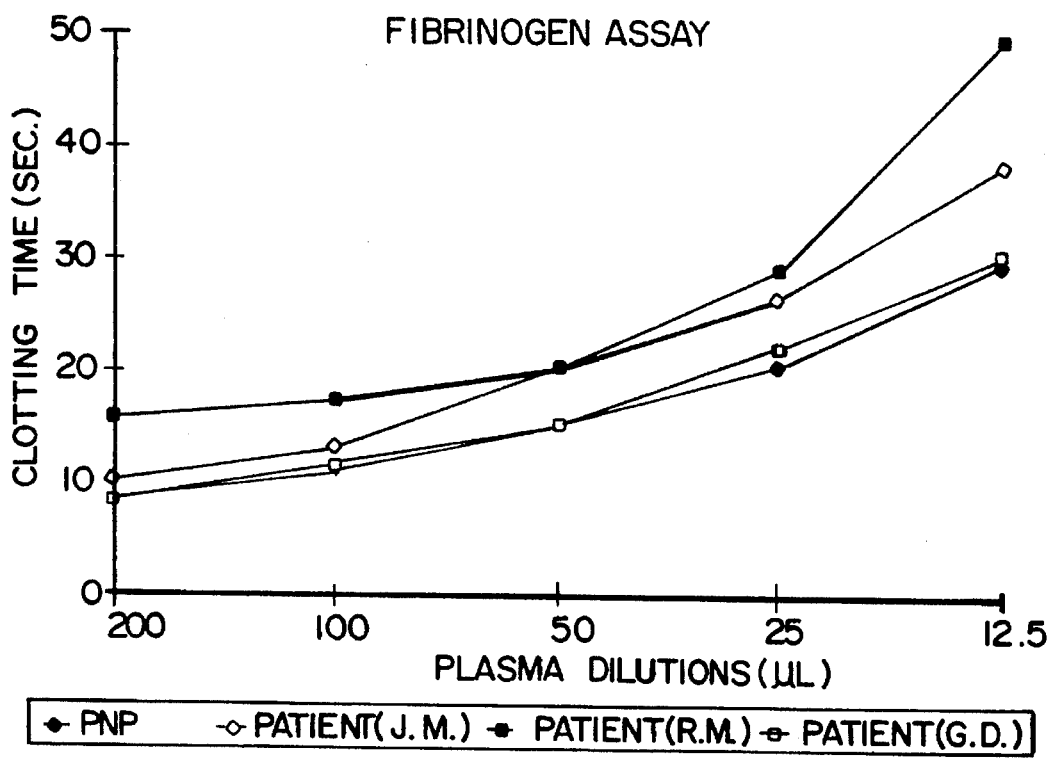

FIG. 20 is a graph showing the results of a fibrinogen assay for various patients.

Figure 21:
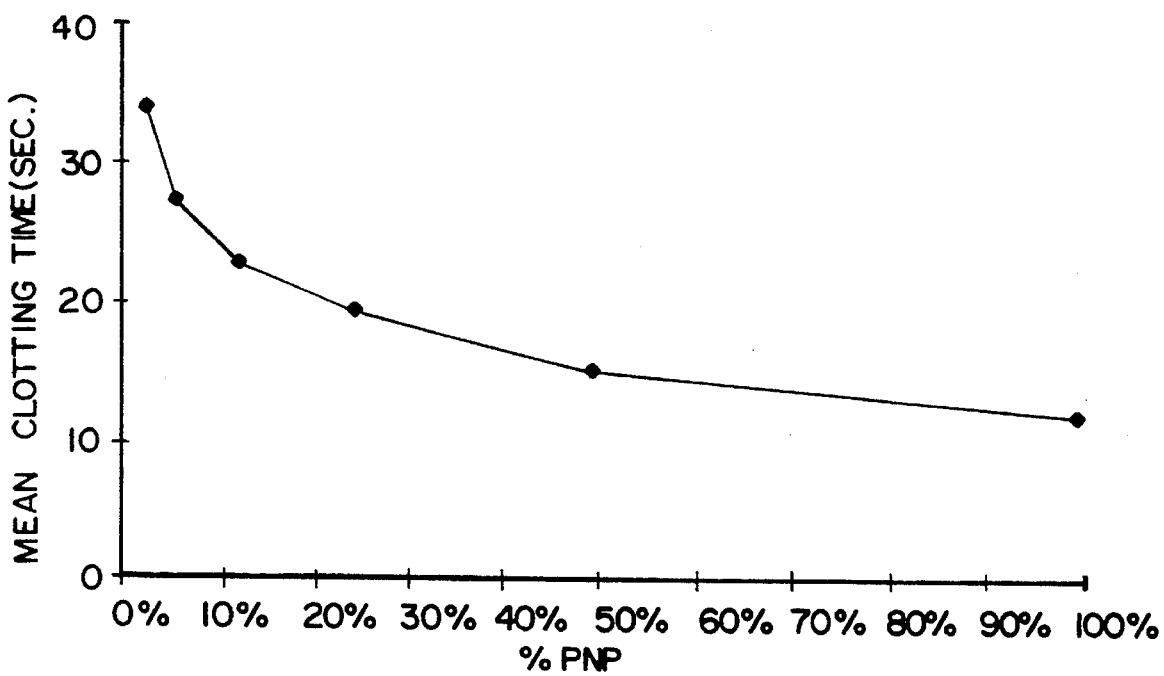

FIG. 21 is a graph showing plasma fibrinogen versus P time.

FIG. 22 is a graph showing the results of testing for antithrombin III.

Figure 23:
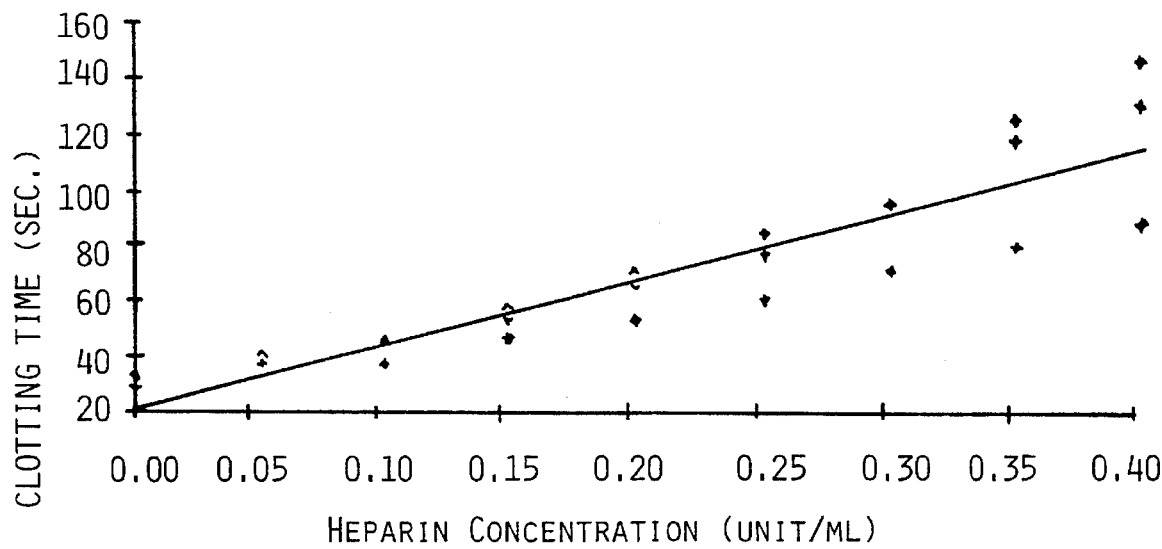

FIG. 23 shows the linear regression clotting time of PNP containing progressive concentrations of bovine lung heparin by the APT assay. The results are representative of those for heparin from other sources.

Figure 24:
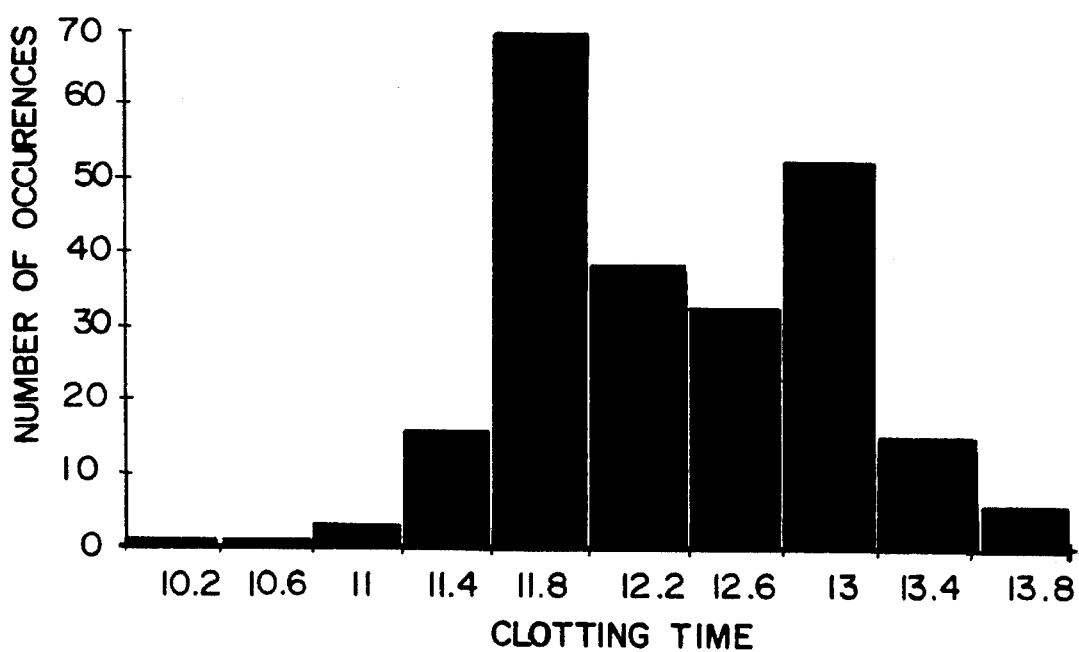

FIG. 24 determines whether 40 percent factor activity was equivalent to 80 percent factor activity for Factor V. In the test, 50 ul single factor genetically deficient plasma was mixed with 50 ul single donor plasma in the PT and APTT assays. From the bar charts it is seen that clotting times by the APTT and PT assays for 40 percent plasma levels of Factors V, VII and VIII are very close to the clotting times of 80 percent levels of the clotting factors.

Figure 25:
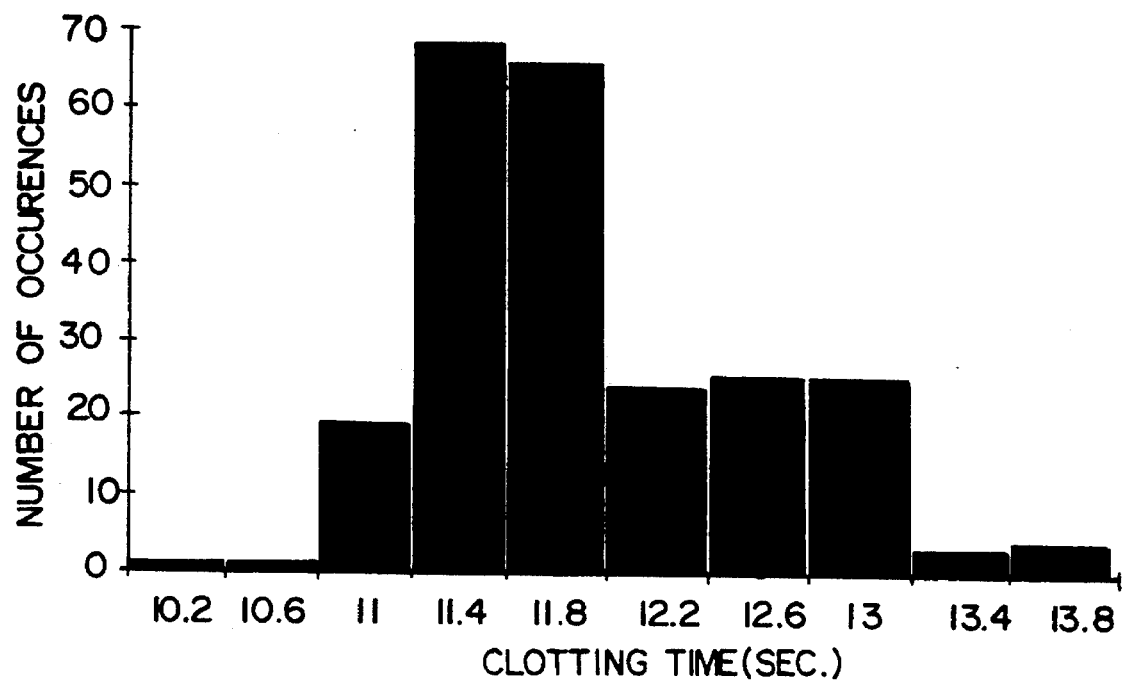

FIG. 25 determines whether 40 percent factor activity was equivalent to 80 percent factor activity for Factor VII. In the test, 50 ul single factor genetically deficient plasma was mixed with 50 ul single donor plasma in the PT and APTT assays. From the bar charts it is seen that clotting times by the APTT and PT assays for 40 percent plasma levels of Factors V, VII and VIII are very close to the clotting times of 80 percent levels of the clotting factors.

Figure 26:
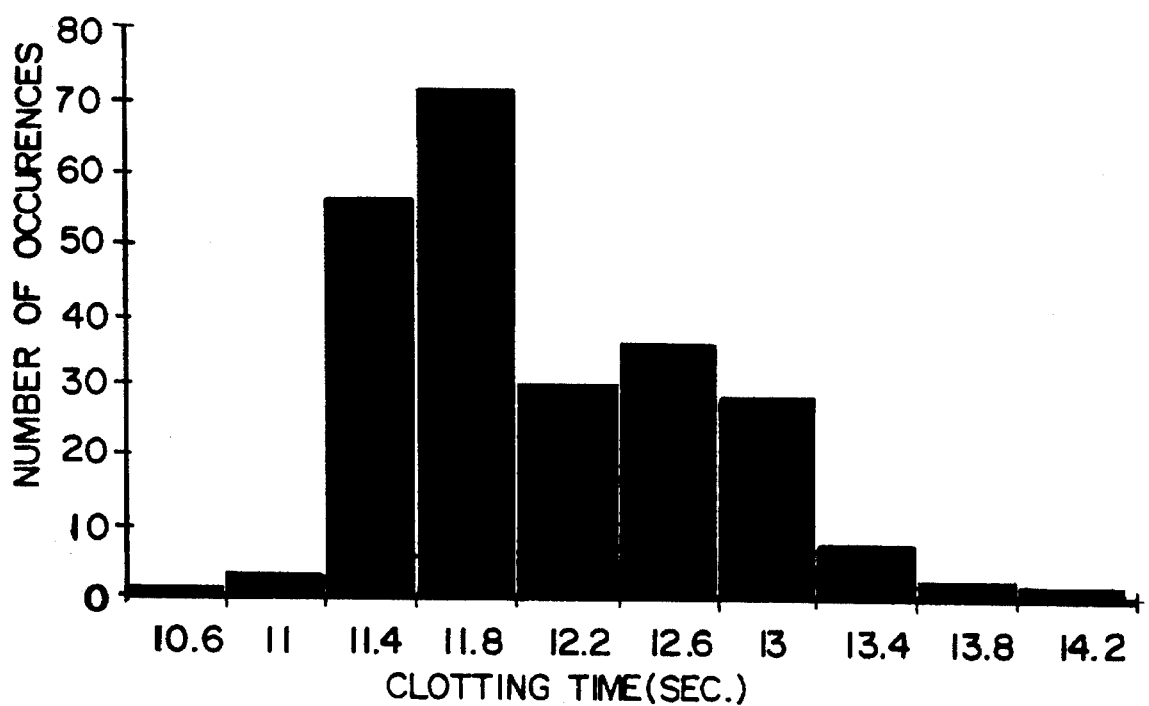

FIG. 26 determines whether 40 percent factor activity was equivalent to 80 percent factor activity for Factor X. In the test 50 ul single factor genetically deficient plasma was mixed with 50 ul single donor plasma in the PT and APTT assays. From the bar charts it is seen that clotting times by the APTT and PT assays for 40 percent plasma levels of Factors V, VII and VIII are very close to the clotting times of 80 percent levels of the cletting factors.

Figure 27:
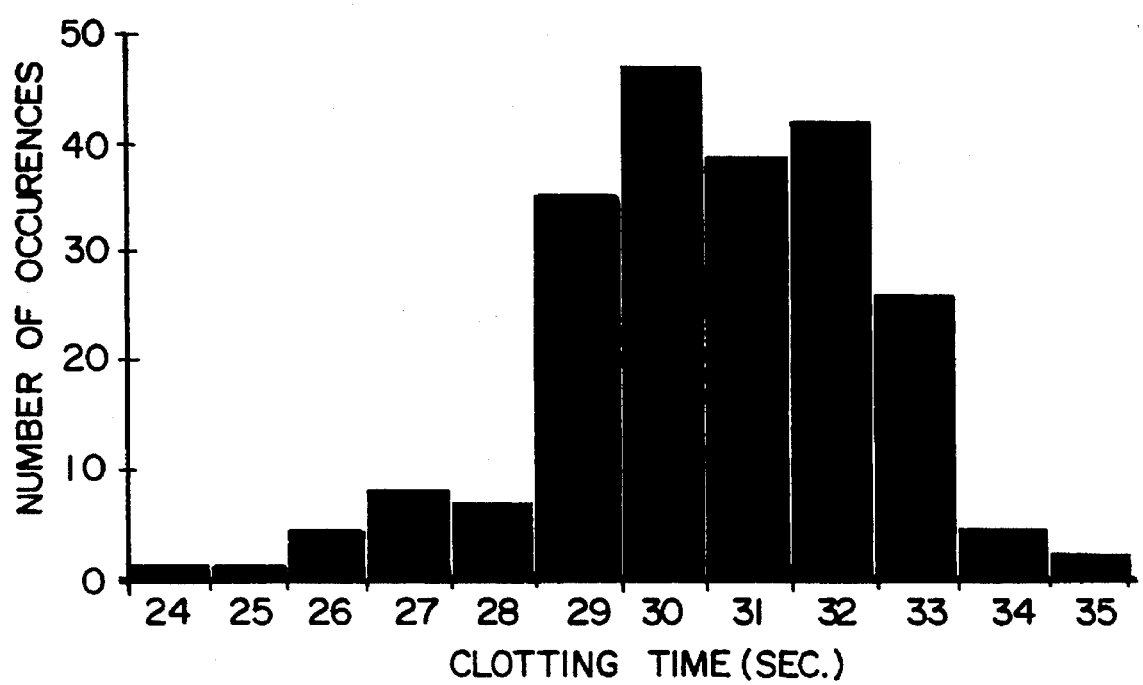

FIG. 27 determines whether 40 percent factor activity was equivalent to 80 percent factor activity for Factor VIII. In the test, 50 ul single factor genetically deficient plasma was mixed with 50 ul single donor plasma in the PT and APTT assays. From FIGS. 24 to 27 it is seen that clotting times by the APTT and PT assays for 40 percent plasma levels of Factors V, VII, VIII and X are very close to the clotting times of 80 percent levels of the clotting factors.

Figure 28:
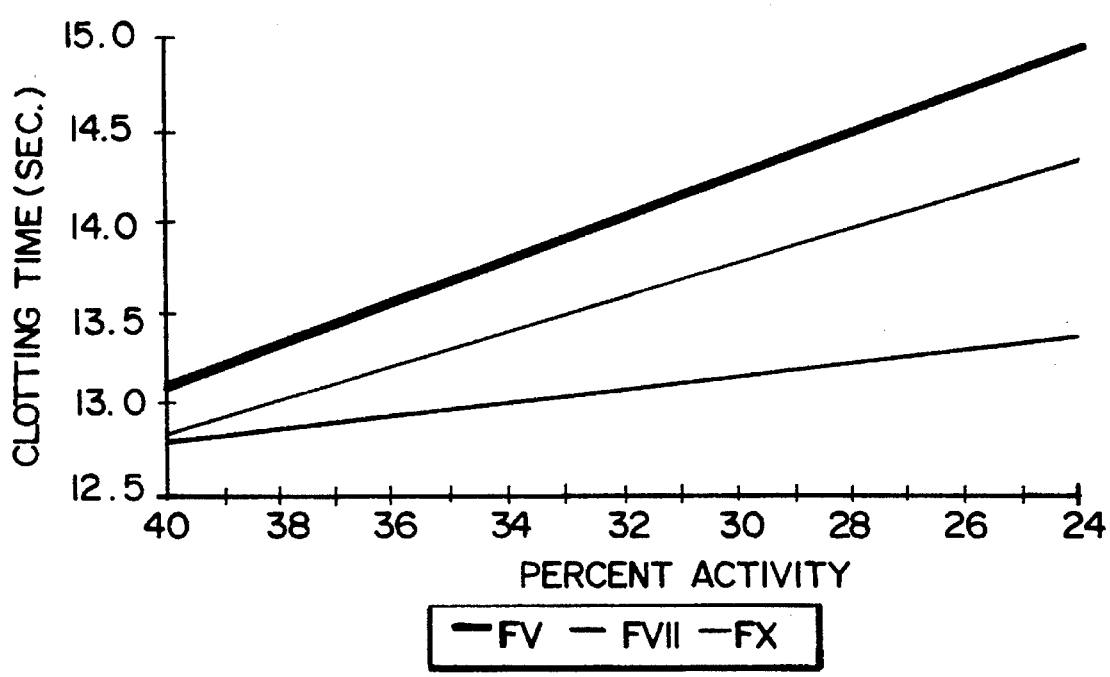

FIG. 28 shows standard curves in factor deficient plasma. It was proved that there is a lack of scientific evidence for use of 20 percent plasma to buffer ratio as equivalent to 100 percent activity. It was shown that there was a loss of activity for FV and FX in the PT and APTT assays at 35 percent plasma concentration. Twenty percent activity is not equivalent to 100 percent for several factors. Yet, factor assays in all hospital laboratory settings are performed on that incorrect assumption.

FIG. 29 shows standard curves for descending ranges of Factors V, VIII, IX, X and XI by the APTT assay.

GENERAL DESCRIPTION

The present invention relates to a method for diagnosing blood clotting disorders in humans which comprises: separately testing sets of a sample of plasma separated from the blood of a patient and sets of a sample of plasma from pooled normal plasma (PNP) from healthy humans for clotting time (CT) by addition of predetermined amounts of prothrombin time reagents (P) to a first set of the sample; activated partial thromboplastin (APT) to a second set of the sample and thrombin (T) to a third set of the sample, charting the results for the patient and the PNP together on a side-by-side basis for P, APT and T and comparing the results with a data base showing normal ranges of CT based upon the PNP for APT, T and P wherein the APT, T and P have been separately prepared in solution to produce a particular standardized clotting time with PNP which is used in all of the testing of the patient plasma; testing for hypercoagulation or bleeding based upon the P, APT and T tests and charting the results; and providing a diagnosis based upon the differences of CT based upon the tests.

Further the present invention relates to a method for diagnosing blood clotting disorders in humans which comprises: separately testing a first set of samples of plasma from a patient and pooled plasma from normal healthy humans (PNP) for the time to coagulate by prothrombin time reagents (P), activated partial thromboplastin (APT) and thrombin (TCT), charting the results together on a side-by-side basis, and comparing the results from the samples with a data base showing abnormal and normal ranges of coagulation times (CT) for healthy humans, wherein the APT, T and P have been prepared in solution to produce particular standardized clotting time with PNP which is used in all of the testing of patient plasma; optionally testing second sets of a sample of the plasma from a patient and PNP by mixing the patient plasma suspected to be genetically deficient in a blood factor selected from the group consisting of Factors V, VII, VIII, IX, X, XI, XII, F1.F and HMWK (HMWK is HMW-kininogen and F1.F is Factor 1 fibrinogin) with a volume factor deficient of a genetic plasma in an amount between about 40 to 60 percent by volume of GFPD to PNP and patient plasma for coagulation by an appropriate one of P, APT or both separately, charting the results together on a side-by-side basis and comparing the results with a second data base showing normal ranges of CT based upon PNP wherein the CT of GFPD is corrected by the PNP and normal patient plasma; optionally testing the samples of the plasma for anti-thrombin III by determining CT for the patient and PNP, charting the results together on a side-by-side basis and comparing the results with an antithrombin III data base showing normal ranges for PNP; optionally testing the samples of the plasma for protein C by determining CT and charting the results and comparing the results with a protein C data base showing normal ranges of CT based upon the PNP; optionally testing the samples of plasma for fibrinogen from the patient plasma and PNP and determining CT for coagulation by T at known dilutions of the plasma, charting the results as CT on a side-by-side basis and comparing the results with a fibrinogen data base showing normal ranges of CT for the PNP; and providing a diagnosis based upon the differences in coagulation times in the tests.

In the present invention the PNP is used to rigidly standardize the CT reagents P, APT and T and are formulated to always produce the same CT with PNP. For T the CT is preferably 8 to 9 seconds. This is 1.2 units per 100 ul of solution. For AP the CT is preferably 26.4 seconds ±2 seconds. For P the CT is preferably 11.6 seconds ±1 second. Generally the tests are conducted in 200 ul of PNP. If this procedure is not followed, the results of the assays will be variable from lot to lot of P, T, and APT and from day to day and the results in the manner of the present invention can not be achieved which relies upon producing the same CT with normal plasma.

It has been found that when PNP is mixed with a Factor deficient plasma, in a volume between about 40 and 60% of the volume of the Factor deficient plasma (GFDF) in a PT, APTT or TCT/TT assay that the PNP will correct the factor deficiency and if it is normal, the patient plasma will correct the factor deficiency of a factor deficient plasma. If there is a particular factor deficiency in the patient plasma it will not correct the GFDF thus showing that the patient plasma is also deficient in this factor. This mixing technique is a basic concept of the present invention. Histograms for FVII, FX and FV by the PT assay and FVIII by the APTT assay are shown in FIGS. 24 to 28.

Diseases associated with hemostatic disorders are broadly categorized into bleeding and thrombosis. Bleeding can be external or internal. Internal bleeding includes the types that manifest under the skin such as hematomas, bruises, purpura and petichiae. Thrombosis can be acute or chronic. The acute form of thrombosis if untreated, will result in severe uncontrollable bleeding. Chronic thrombosis can be caused by deranged protein coding or by environmental factors.

To investigate the pathogenesis of bleeding and thrombotic diseases a multitude of standardized procedures were developed. Some are complicated, with a high degree of sophistication and can be carried out only in research laboratories. Others are relatively simple and suitable for clinical testing.

FIGS. 1 to 8 show the diagnosis of various diseases and the CT for normal and abnormal patient plasma by the APT, PT and T tests. These tests are performed and charted as shown in FIGS. 10 to 18. The individual assays are for factor deficiency, inhibitors, contact phase antithrombin III, protein C, and fibrinogen as well as other standard assays as shown in the charts.

SPECIFIC DESCRIPTION

Routine Assays

There are several well established screening procedures of a very general nature which are ordered routinely on individuals who present for the first time with a bleeding disorder.

(1) The Tourniquet Test (Rumple Leede Test). This is a non-invasive, easy to perform procedure to identify capillary fragility. It is performed by applying a blood pressure cuff for 20 to 40 minutes and applying a 40 mm Hg pressure. In fact, it is the only available testing procedure for the blood vessel component of the hemostatic system. Blood vessel disease is the least commonly encountered hemostatic abnormality. It is frequently seen associated with viral infections, drug induced vasculitis, and collagen diseases such as lupus erythematosus and others. It is also frequently seen in the elderly.

(2) Platelet Count. A platelet count of 50,000 per cubic milliliter of blood ensures adequate hemostasis unless challenged by stressful conditions such as trauma, surgery or childbirth. Platelet counts of 10,000 per cubic milliliter of blood are dangerously low and may lead to spontaneous hemorrhage. Thrombocytosis is a platelet count above 500, 000 per cubic milliliter. Thrombocytosis predisposes to thrombosis in most cases. In myeloproliferative disorders platelet counts may reach 1 million per cubic milliliter. In such conditions platelet functions are defective and thrombocytosis is associated with excessive bleeding rather than thrombosis.

(3) Bleeding Time Tests. The Duke and Ivy time bleeding procedures are technically difficult to perform. Adequate standardization is essential for the interpretation of the results. In expert hands a normal bleeding time of greater than 15 minutes is frankly abnormal and indicates:

Severe impairment of platelet functions of genetic or acquired origin.

Very low blood levels of von Willebrand Factor.

Afibrinogenemia and severe Factor V deficiency.

A bleeding time greater than 8 minutes and less than 15 minutes is more difficult to interpret. A moderately low plasma level of vWF is by far the most common underlying pathogenesis. Antiplatelet drugs, lupus-like inhibitors and Factor XI deficiency should be considered in the differential diagnosis.

(4) Prothrombin Time (PT). The PT is a screening test to identify coagulation abnormalities of the extrinsic and common pathways and fibrinogen. This test is performed by mixing tissue thromboplastin/calcium chloride solution (TTP/CaCl$_2$) with the plasma. Oral anticoagulant medication is the most frequent cause of prolonged PT. The only abnormality that causes a prolonged PT and no changes in the other screening tests is a Factor VII deficiency. The PT is sensitive to slight decreases in plasma levels of Factor V.

(5) Activated Partial Thrombo-Plastin Time (APTT). The APTT is a screening test to identify coagulation abnormalities of the contact phase and the intrinsic and common pathways of plasma activation. This test is performed by mixing activated partial thrombin reagent (APTT) with the plasma. The APTT is not sensitive to fluctuation in plasma fibrinogen levels. Of conditions that cause prolongation of the APTT, the most frequent is contamination of plasma with heparin. Other conditions are Factors VIII and IX deficiencies as well as lupus-like anticoagulants. A factor XII deficiency of less than 1% gives an APTT of 260 to 300 seconds, while deficiencies of Factor VIII or IX of less than 1% will give a more modest increase of 78 to 82 seconds in the APTT.

(6) Thrombin Clotting Time/Thrombin Time Assay (TCT/TT). TCT or TT is the same assay given two slightly different names. TCT/TT measures the time taken by exogenously added thrombin to proteolyze plasma fibrinogen and to form a clot. TCT/TT assays are not standardized by the prior art. Each laboratory determines the activity (strength) of thrombin to be used in the assay. It is customary to adjust the thrombin activity to give a clotting time of 8 to 9 seconds with 0.2 ml citrated pooled normal plasma (PNP). This is equivalent to 1.2 NIH units of thrombin activity.

The usefulness of TCT/TT as a screening assay is underestimated since it is not specific for any disease condition. However, routine use of TCT/TT alongside the PT and APTT is invaluable to differentiate efficiencies of the intrinsic pathway from heparin, and separate lupus-like anticoagulants from afibrinogemia and paraproteinemia.

(7) Euglobulin Lysis Time Test. This is a crude but effective screening test for accelerated fibrinolysis. If the clot dissolves much faster than the control plasma, it is correct to attribute the patient's condition to a deficiency of the major inhibitor of plasmin, alpha-2-AP or to a deficiency of the major inhibitor of plasmin, alpha-2-AP or to a deficiency of activated Factor XIII, the fibrin cross linking transglutaminase. The concentration of alpha-2-AP in plasma is half the capacity of plasma for forming plasmin. Therefore, conditions of accelerated fibrinolysis do not necessarily imply a genetic deficiency of alpha-2-AP, but could mean a transient depletion of the inhibitor.

FIG. 1 shows the possible diagnosis based upon the AP, T and P tests. All of these tests are performed if there is any abnormal bleeding or a thrombosis.

Other Assays:

(8) Fibrinogen Assays

The unique features of this assay are:

1) it is a qualitative as well as a quantitative thrombin time clotting assay;

2) serial dilutions of patient and control plasma are performed simultaneously and clotted with thrombin;

3) fibrinogen in PNP has been quantified by Lowry's assay; and

4) Slopes of curves for control PNP and patient plasma are compared. Calculations for patient fibrinogen levels are read off a regression line. The prior art assays:

Prior Art Assays:

1) are based on Clauss method (citation).

2) evaluated patient fibrinogen duplicate clotting times of one plasma dilution. Calculations are made from a semilogarithmic plot of the regression line of a standard curve performed with purified fibrinogen.

Clinically, the most significant fibrinogen disorders result from:(a) impairment of the velocity with which fibrinogen converts to fibrin and coagulates in plasma; (b) increases or decreases of levels of circulating fibrinogen.

Determination of fibrinogen has, throughout the years, been performed with a variety of methods, each in itself burdened with its own inherent limitations. A brief listing of various methods includes the turbidimetric estimation of fibrinogen after salting out procedures, estimation of fibrinogen by zone electrophoresis, spectrophotometric assays of the purified protein, assays of fibrinogen as fibrin after coagulation, and gravimetric and heat precipitation.

For clinical testing in the present invention, two procedures are performed:

A. Thrombin Clottable Fibrinogen (TCF) Assay, and

B. Heat Precipitatable Plasma Fibrinogen (HPPF) determination by Lowry's Assay.

A. Thrombin clottable fibrinogen assay (TCF)

In the TCF Assay, a thrombin solution (1.2–1.5 NIH units; CT 7–8 secs) is added to serial dilutions of patient plasma and pooled normal plasma (PNP). The dilutions are done with defribilated PNP. Enzyme concentration is always constant; substrate is serially diluted. The defibrilated PNP will be partially corrected by the normal PNP on a reproducible basis. The velocity of fibrinogen conversion and fibrin polymerization is recorded on a coagulation analyzer. Two graphs are sketched by plotting the points for the clotting times of the patient and PNP as shown in FIGS. 19 to 21. The plasma dilutions are preferably on the x-axis and the clotting times in seconds on the y-axis. By finding the slope and y-intercept of both lines of the graph the following information can be derived:

(1) If the slopes of the line of the patient and the control are parallel; and the y-coordinates (y-intercept mean clotting time) are at the same place on the axis, the diagnosis is that levels of biologically functional fibrinogen are within the normal range.

(2) If the slopes of the line of the patient and the control are parallel but the y-coordinate of the patient is translated upward (more prolonged clotting time) the diagnosis is that levels of biologically functional fibrinogen are decreased.

(3) If the slopes of the line of the patient and the control are parallel but the y-coordinate of the patient is translated downward (shorter clotting times) the diagnosis is that levels of biologically active fibrinogen are increased.

(4) If the graph of the patient has a different slope from that of the control the only possibilities are: heparin or an abornmal fibrinogen. Heparinized plasma will give a false positive result for dysfibrinogenemia.

To rule out the interference by heparin, 1 ml of the patient's plasma is reacted with a heparin absorbent chemical (Hepasorb™) (need source) for 10–20 minutes. The absorbant approach is less costly and just as effective as the better known reptilase test (citation).

Following treatment of patient plasma with absorbant, the TCF assay is repeated. If the slopes of the graph continue to be different, an abnormal fibrinogen is verified by HPPF determination. The diagnostic findings for dysfibrinogenemia are: discrepancy in levels of fibrinogen obtained by the HPPF assay (higher) and the TCF assay (lower).

Determination of Fibrinogen Levels

The points for the fibrinogen levels and clotting times of control plasma are entered on the keyboard of a scientific calculator. The slope, y-intercept and the correlation coefficient of the linear regression line are obtained. To calculate the level of fibrinogen in the patient's plasma enter a y'-coordinate (a clotting time for one of the patient plasma dilutions) into the keyboard. The calculator will find and print the corresponding x-coordinate (control plasma (PNP) dilution) equivalent to the fibrinogen level for the patient.

Materials and Methods

PREPARATION OF PLASMA

Pooled Normal Plasma (PNP)

PNP is prepared by pooling human citrated plasma obtained from 40 healthy volunteers. The PNP can be stored in 0.5 ml aliquots in small conical plastic tubes at −70° C. and has a stability of 5 years.

Defibrinated Pooled Normal Plasma (Defibr PNP)

Pooled Normal Plasma (PNP) for defibrination is prepared by pooling ten units of outdated citrated human plasma. The pooled plasma is aliquoted into 25 ml conical plastic centrifuge tubes. Plasma is defibrinated by placing the plastic centrifuge tubes containing the plasma in a water bath heated to 56° C. The temperature of the plasma is brought to 56° C. and maintained at that temperature for 5 minutes. This process denatures fibrinogen. Centrifugation at 2,000 rpm for 15 to 20 minutes then precipitates the denatured fibrinogen to the bottom of the tubes.

The supernatant is the defibrilated PNP that is used as the diluent in the TCt Assay. A thrombin clotting time is performed to verify the completeness of removal of fibrinogen. Packaging is by placing 1.5–2 ml of defibrilated PNP into plastic tubes. Storage is at −70° C. and the stability is 10 years.

Chemical estimation of fibrinogen:

The denatured fibrinogen pellet is reconstituted in 25 ml distilled water. A Lowry's Assay is performed as described hereinafter. The concentration of fibrinogen in plasma is expressed in milligrams per deciliter.

Patient Plasma

Blood is collected in sodium citrate. Quantity: 5 ml blood to yield about 2 ml plasma. Patient's plasma is not debrinated, and is used in the assay as whole decalcified plasma.

REAGENTS

Tissue Thromboplastin: prepared from rabbit brain.
Calcium Chloride: 0.02M.

Activated Phospholipid Reagents: activating agents can be ellagic acid, kaolin, silica or soybean extract, etc.

Thrombin Reagent: the powdered thrombin is reconstituted in a solution of $CaCl_2$ 0.1M. Clotting activity of thrombin is adjusted to 1.2 unit/per 100 ul which will give when added to 200 ul PNP a clotting time of 8–9 seconds.

EQUIPMENT

Fibrometers or photo optical systems.
Assay Procedures

EXPERIMENTAL PROCEDURES

Plasma Dilutions

Two duplicate sets of fibrocups or cuvettes are labeled 1 to 6. Pipette in all the cuvettes or fibrocups 200 ul defibrilated PNP. Label one duplicate set PNP and the other duplicate set Patient.

In #1 PNP pipette 200 ul PNP perform a serial dilution of PNP in Defibr PNP. Discard 200 ul from #6.

In #1 Patient pipette 200 ul patient plasma. Perform a serial dilution of patient plasma in Defibr PNP. Discard 200 ul from #6.

Measurement of Clot Formation

A. A prothrombin time (PT) assay or a thrombin clotting time (TCT) assay can be performed. The clotting times are recorded on the report chart (FIG. 7).

Analysis of the Properties of Plasma Fibrinogen

This can be performed on a scientific calculator, on a personal computer with graphic capabilities, or on a photo optical coagulation analyzer with graphics capabilities.

Enter on the keyboard two separate sets of results:

y: clotting time of plasma dilutions of PNP.

y': clotting time of plasma dilutions of patient.

x: plasma dilution of PNP x': plasma dilution of patient

FIG. 20 shows the results of the assay with thrombin. FIG. 21 shows the results with prothrombin.

B. Heat precipitatable plasma fibrinogen determination by modified Lowry's Assay.

Test Procedure:

1. Percent plasma fibrinogen dilutions are made in the following way:

100% PNP is pooled normal plasma.

50% PNP is 1 ml 100% PNP and 1 ml distilled water.

25% PNP is 1 ml 50% PNP and 1 ml distilled water.

12.5% PNP is 1 ml 25% PNP and 1 ml distilled water.

6.2% PNP is 1 ml 12.5% PNP and 1 ml distilled water.

3.1% PNP is 1 ml 6.2% PNP and 1 ml distilled water.

2. Dilution sets are made up of 1 ml of each plasma fibrinogen dilution. Dilution sets are then incubated separately in a 56° C. water bath. Two dilution sets are incubated for 5 minutes; another two dilution sets are incubated for 30 minutes. Centrifugation of each dilution set at 2,000 rpm for 15 minutes immediately after incubation yields the fibrinogen precipitate.

3. Each precipitate is then reconstituted with 1 ml distilled water and determined by Lowry's Assay which is described hereinafter.

In the Lowry's assay, proteins including fibrinogen (5–100 micrograms sensitivity range) are measured with the Folin Phenol Reagent after alkaline copper treatment. Following alkaline treatment, free tyrosine and tryptophan residues react with copper, resulting in a 3- to 15-fold increase in color. This reaction is complete in 5–10 minutes at room temperature. The copper-treated protein will reduce the phosphomolybdicphosphotungstic (Folein) reagent. The final color is greatly enhanced. This reaction is complete in 30 minutes at room temperature.

Reagents

Reagent A: 2% $Na_2CO_3$ (10 g/500 ml) in 0.10M NaOH (2 g/500 ml).

Reagent B: 2% Na tartrate and 1% $CuSO_4$ (1:1 volume).

Reagent C: Alkaline Copper solution: 100 ml A and 2 ml B. (Discard after 1 day).

Reagent E: Folin reagent 2N diluted 1:2 in distilled water to make 1N solution.

Procedure:

The sample is 0.2 ml to which 1 ml of Reagent C is added and vortexed immediately.

The sample with Reagent C sits at room temperature for 10 minutes and then 0.1 ml of Reagent E is added and vortexed immediately.

The sample then sits at room temperature for 30 minutes and is then read on Spectrophotometer at 750 nm.

Calibration Curve:

The curve prepared by dissolving 1 mg albumin in 1 ml distilled water (1 microgram/1 microliter).

Blanks:

The blanks are:

Distilled water 0.2 ml

Reagent C: 1 ml

Reagent E: 0.1 ml

PROCEDURE FOR CALIBRATION CURVE

Albumin 1 mg/1 ml (1 ug/1 ul)

5 ul 10 ul 20 ul 50 ul 100 ul

The albumin solution is q.d. to 0.1 or 0.2 ml in distilled water or buffer.

(Disposable glass tubes and duplicate samples).

Blanks: 0.1 to 0.2 ml distilled water or buffer.

Protein sample: 5–10 ug sensitivity range.

Add 1 ml of Reagent D and vortex immediately. The sample then sits at room temperature for ten minutes.

PROCEDURE

Prepare Folin reagent.

Pipette 3 ml Folin Reagent and 3 ml distilled water to produce 6 ml. Combine in small beaker. Add 0.1 ml Folin Reagent to:

(1) Standard curve; (2) Blank; and (3) Protein samples and vortex immediately.

The sample then sits for 30 minutes at room temperature and the optical density of samples is read on a spectrophotometer (which can be single or double beam).

SPECTROPHOTOMETER

Set at 750 nm (visible)

1. Warm instrument for 30 minutes prior to use.
2. Calibrate with BLANK
3. Use quartz cuvettes (washed in chromerge acid(?))
4. Read optical density (O.D.) of calibration curve)
5. Read O.D. of protein samples
6. Construct on calculator linear regression for calibration curve.

Estimation of slope, intercept and protein concentration of unknown samples can be obtained by entering the:

Concentration (x values) of albumin used in the calibration curve, followed by entry of O.D. (y values) obtained on spectrophotometer.

Procedure:

---

Press: 2nd Pgm 1 SBR CLR to clear the calculator.
Then
 Press: Value of x (5 mg)
 Press: x = tg Then
 Press: value of y (O.D. reading)
 Press: 2nd + Then

---

Repeat process for values of x: 10 micrograms, 30 micrograms, 50 micrograms, 100 micrograms.

To calculate:

The y intercept of the line fitted to the data points, PRESS 2nd OP 12. The slope of the line, PRESS 2nd OP 12 x≅t. The correlation coefficient, PRESS 2nd OP 13. The linear estimate of x on the regression line, enter y value on the keyboard, followed by 2nd OP 15.

The amount of fibrinogen is related to an equivalent amount of the albumin and is expressed in mg/ml. The modified Lowry's assay produces results which are compared to the TCF assay.

The results are charted as set forth in FIG. 16.

(9) Inhibitor Assays

Until about five years ago the best known of the coagulation inhibitors were those that developed in hemophiliacs in response to Factor VIII replacement therapy. Nowadays the lupus-like anticoagulant or lupus-like inhibitor has taken in the scientific literature a place of considerable importance. There are several types of lupus-like inhibitors.

Some are purely in vitro phenomena. They are easily identified in phospholipid-dependent coagulation tests. They cause significant prolongation of the clotting times of normal plasma when equal amounts of lupus inhibitor plasma are added to the reaction mixture. Also, plasma with lupus inhibitor does not correct the prolonged clotting times of assorted single factor deficient plasma reagents. Significantly in vitro type lupus inhibitors are neutralized by Platelet Factor III activity.

Other lupus inhibitors have been found to interfere with the activation of coagulation factors and impair the in vivo biological function of these factors. With this type of lupus inhibitor a bleeding diathesis may develop under challenge to the hemostatic system. More often however, they tend to cause an increase in the susceptibility to thrombosis. Lupus inhibitors directed against the biological activity of Factors V, VIII and prothrombin have been identified. These were exclusively present in elderly females with connective tissue disorders. Inhibitors have been identified in other categories of individuals and in association with a variety of diseases. This type of lupus inhibitor is best identified in mixing studies with PNP and single factor deficient plasma reagents as indicated in the chart (FIG. 3) labeled "Inhibitor Screen". The method for the Inhibitor Screen is very simple. Mix 50 ul PNP or single deficient plasma reagent and perform a PT or an APTT assay. The activator substance in the APTT assay should be kaolin, soybean extract, silica, never ellagic acid. If evidence points to a specific coagulation factor inhibition, an inhibitor assay is performed.

The only difference between in vivo lupus-like anticoagulants directed specifically against the activity of a coagulation factor and the inhibitors that develop in hemophiliacs is our lack of our understanding of the site of action of lupus-like anticoagulants. The inhibitor Assay can accurately measure the antibody titer of inhibitors to Factors VIII or Factor IX that develop in hemophiliacs as well as the in vivo lupus-like anticoagulants. By definition an antibody titer is the amount of antibody that can bind to one unit of antigen. Unit can be in measures of weight or activity. In our assay we measure the inhibition 1 unit of activity of a single coagulation factor.

INHIBITOR ASSAY

Specificity of the inhibitor assay is for:

1) Inhibitors that develop in hemophiliacs and other individuals. These types of inhibitors are antibodies directed specifically against a procoagulant factor.

2) Lupus like inhibitors. These are inhibitors directed specifically against phospholipids. These antibodies are recognized by their effect on the clotting times of the APTT assay. Two types of lupus like inhibitors can develop:

i) a non-specific type that reacts in vitro with phospholipid reagents to inactivate them. These inhibitors do not cause bleeding problems.

ii) a specific type that reacts with platelet phospholipids and prevents complex formation and assembly. These inhibitors can cause serious bleeding problems.

The principle of the inhibitor assay for inhibitors that develop in hemophiliacs and other individuals is a direct inhibitor assay similar to the passive hemaglutination assay. The end point of this assay determines the amount of factor activity inhibited by a known quantity of patient plasma. Thereby calculations are made as to how much factor concentrate is needed to overcome the inhibitor.

The principle of the assay for lupus like inhibitors is to mix in equal proportions of the patient's plasma and a control plasma. If the prolonged clotting times by the APTT assay are corrected, a lupus like inhibitor can be ruled out with certainty. To provide proof for a lupus like inhibitor, the patient's plasma is mixed in equal proportions with Factor VIII deficient plasma and an APTT assay is performed. If the prolonged clotting time by the APTT is not corrected, evidence is very strong of a lupus like inhibitor.

Reagents:
  Citrated pooled normal plasma (about 1 ml).
  Factor VIII deficient plasma (about 2 ml)
  Activated Partial Thromboplastin Reagent ("Actin™"), purchased from American Dade (ellagic acid), or Helena™ APTT Reagent (kaolin) CaCl$_2$ (0.02M)
  MLA pipettes and pipette tips: 200 microliters, 50 microliters, 30 microliters, 20 microliters and 10 microliters.

Method

Step 1:
Prepare 5 tubes, label 1–5

Tube # Plasma Mixture (Antigen dilution, FVIII deficient)
1 200 microliters PNP
2 200 microliters PNP+200 microliters FVIII deficient. Mix.
3 Add 200 microliters from tube 2+200 microliters FVIII deficient. Mix.
4 Add 200 microliters from tube 3+200 microliters FVIII deficient. Mix.
5 Add 200 microliters from tube 4+200 microliters FVIII deficient. Mix and discard 200 microliters.
6 200 microliters patient's plasma.

Step 2: Add inhibitor to antigen dilution.
Tube 1 0.16 unit FVIII/200 microliters, add 50 microliters patient plasma.
Tube 2 0.08 unit FVIII/200 microliters, add 30 microliters patient plasma.
Tube 3 0.04 unit FVIII/200 microliters, add 20 microliters patient plasma.
Tube 4 0.02 unit FVIII/200 microliters, add 10 microliters patient plasma.
Tube 5 0.01 unit FVIII/200 microliters, add 10 microliters patient plasma.

Control: Standard curve of PNP in Factor VIII deficient plasma.
Label tubes 1–10.
80% 1. 200 microliters PNP
40% 2. 200 microliters PNP+200 microliters FVIII deficient. Mix.
20% 3. Add 200 microliters from tube 2 to 200 microliters FVIII deficient. Mix.
10% 4. Add 200 microliters from tube 3 to 200 microliters FVIII deficient. Mix.
5. Add 200 microliters from tube 4 to 200 microliters FVIII deficient. Mix.
2.5% 6. Add 200 microliters from tube 5 to 200 microliters FVIII deficient. Mix.
1.2% 7. Add 200 microliters from tube 6 to 200 microliters FVIII deficient. Mix.
0.6% 8. Add 200 microliters from tube 7 to 200 microliters FVIII deficient. Mix.
0.3% 9. Add 200 microliters from tube 8 to 200 microliters FVIII deficient. Mix.
0.1% 10. Add 200 microliters from tube 9 to 200 microliters FVIII deficient, mix and discard 200 microliters.

Step III:
Incubation: Plasma mixtures are incubated for 1 hour at 37° C.

At the end of the incubation period, 100 microliters of plasma mixture from each tube is added to 100 microliters prewarmed activated partial thromboplastin reagent in fibrocups. After 3 minutes, the mixture is clotted with 100 microliters CaCl$_2$ 0.02M.

Calculations

Follow the instructions outlined on the report chart FIG. 12. Results are interpreted as follows:

1. A powerful inhibitor will overcome and neutralize all of the activity present in all plasma dilutions, and consequently one is unable to determine the antibody titer. In this instance the test should be repeated using 20 ul, 10 ul, 5 ul and 1 ul of patient's plasma while preserving the same initial factor activity in the plasma mixture.

2. In another case, 1 ml of patient's plasma inhibits 3 units of Factor VIII activity. Since an adult human of average weight and height will have 3 liters of circulating plasma, it is probable that 9,000 units Factor VIII concentrate will neutralize the inhibitor in vivo.

3. A third example is that of a lupus-like anticoagulant. When tested in this system it will neutralize any of the plasma activity in the mixture. (10) Antithrombin III Assays The unique features of the Antithrombin III assay are: 1) it is a clotting assay; 2) the plasma is not diluted and is defibrinated; 3) the thrombin used in the assay is standardized; 4) heparin added to the assay mixture is standardized; 5) fibrinogen used in the assay is ATIII deficient plasma fibrinogen (200 micrograms per 100 microliters); 6) calculations are based on molecular interaction of ATIII and thrombin in the inactivation process.

In all other ATIII clinical clotting assays: 1) plasma is variably diluted; 2) thrombin activity is not recorded or has not been determined; 3) heparin is standardized; 4) purified fibrinogen is used for the end point; 5) calculations are based on a standard curve of thrombin fibrinogen interaction.

ATIII levels are decreased in hereditary ATIII deficiency, intravascular coagulation, hepatitis and hepatic cirrhosis and chronic nephritis. Significant laboratory findings in acute disseminated intravascular coagulation are low levels of ATIII activity measured by clotting assays, low platelet count, and decreased levels of fibrinogen. Hereditary ATIII deficiency is characterized by reduced ATIII activity and normal or reduced concentrations of ATIII measured by immunological assays. Other hemostatic parameters are normal.

In clinical laboratories, both clotting and amidolytic assays are used to evaluate the heparin cofactor activity of ATIII. It has been found that ATIII selectively inhibits the clotting activity of thrombin. In other words, when ATIII first forms a complex with thrombin the inhibitor binds the enzyme at the fibrinogen binding site so that even though the clotting activity of thrombin is inhibited, complexed thrombin has the ability to hydrolyze chromogenic substrates. It has been found that the non-clotting forms of thrombin or "autolyzed thrombins" (beta and gamma thrombin) also form complexes with ATIII. In commercial thrombin preparations, the autolyzed thrombins are present in higher proportion than the clotting thrombin "autolyzed thrombins" have the ability to hydrolyze chromogenic substrates as well as to bind ATIII but do not hydrolyze fibrinogen. Therefore, chromogenic substrate assays measure clotting thrombin forms, thrombin complexed with ATIII as well as autolyzed thrombins. The use of such assays in clinical testing is questionable. The clinical significance of ATIII lies in its ability to inhibit the clotting form of thrombin from hydrolyzing fibrinogen to fibrin.

ATIII levels are measured in the present invention by a clotting assay and an immunologic assay. Chromogenic substrate assays are never used.

To devise an assay to measure the heparin cofactor activity of ATIII in plasma, several very important facts about the effect of heparin on coagulation proteins were taken into account.

Heparin sodium is a mixture of active principles having the property of prolonging blood clotting. The route of administration is intravenous or subcutaneous. Its mode of action is to bind to ATIII. The greater impact of heparin is its in vivo effect on ATIII. This effect is known as the anticoagulant effect of heparin. The discovery of heparin-ATIII interaction provided an explanation for the long-known action of heparin. There is evidence that heparin interacts with ATIII by electrostatic binding to lysine residues of the ATIII molecule. In the presence of heparin, the preferential target of ATIII appears to be thrombin. Some subspecies of heparin may enhance the interaction of ATIII with Factor Xa more than with thrombin or vice versa. When formation of the ATIII-thrombin complex has occurred, heparin readily dissociates from the complex. Thus, it acts as a catalyst of the neutralizing process.

However, the following facts though less well known are equally important.

1. In vitro heparin has not one but two actions on blood coagulation. The less known one is a direct inhibitory effect. Heparin inhibits thrombin and Factor Xa by a direct effect that is due to electrostatic attraction. The inhibition involves the formation of reversible complexes that interfere with the procoagulant effect of both enzymes. Thus heparin has an anticoagulant and antithrombotic effect. The antithrombotic effect of heparin is one of the side effects of heparin therapy.

2. At low heparin concentration, fibrinogen acts as an antithrombin, apparently due to an induced change in the charge of fibrinogen by heparin. This effect is absent in defibrinated plasma and in serum and is significant when the ATIII/heparin cofactor activity of plasma is evaluated.

For clinical testing two procedures are performed:

ATIII/heparin cofactor activity assay.

Counter electrophoresis or cross over.

Immunoelectrophoresis (cross over IEP) immuno assay.

In the ATIII/Heparin Assay:

(1) Test plasma (patient and PNP) is heat defibrinated. This is done to eliminate the effect of fibrinogen on heparin.

(2) Low concentrations of heparin are used: 0.3–0.4 unit/ml. The purpose is to eliminate the direct effect of heparin on thrombin.

(3) Patient and control PNP are never diluted. Again, here the purpose is to eliminate the direct effect of heparin on thrombin. When plasma ATIII is greatly diluted thrombin inhibition will occur as a result of inactivation by ATIII but also as a result of direct inactivation by heparin. Electrostatic binding of the negatively charged heparin to the active site of the thrombin will prevent the enzyme from hydrolyzing fibrinogen. Thus falsely high values for ATIII levels can be obtained.

(4) Thrombin concentration is calculated to be less than plasma ATIII level in the test sample.

PREPARATION OF REAGENTS

1. Patient plasma and control PNP are heat defibrinated by the method described in the fibrinogen assay.

A thrombin solution (1.2 to 1.5 NIH units/100 ul) to give a clotting time of 7–8 seconds when added to 200 ul PNP is prepared in 0.1M $CaCl_2$ in one single 15 ml batch. Thrombin is not frozen and is stored in a plastic tube at 4° C. in the refrigerator. The activity lasts for over 3 to 4 months or even longer if properly handled. Small aliquots for the assay are used at room temperature.

3. A heparin solution is prepared in distilled water as follows: take from the stock solution one unit of heparin. Add this one unit to 10 ml distilled water, mix gently. Heparin concentration is 0.1 unit/100 ul. To titrate the heparin activity suitable for the assay the following should be done.

a. take 5-6 fibrocups or cuvettes and place 200 ul PNP.

b. take MLA pipettes calibrated 20, 30, 40, 50, 60 ul.

c. add 20 ul heparin solution to plasma in fibrocup and clot with thrombin. Record clotting time. Repeat with 30 ul, 40 ul, etc.

d. ideal clotting time for the assay is 30-45 seconds.

ASSAY PROCEDURE

The results are reported in the chart (FIG. 14).

1. 100 ul defibrinated patient plasma are placed in 4 fibrocups.

2. 100 ul defibrinated PNP plasma are placed in 4 fibrocups.

3. Add heparin to 2 fibrocups. Add thrombin then clot with PNP (100 ul). Record clotting time.

4. Other 2 fibrocups, add thrombin then clot with PNP.

CALCULATIONS

The stoichiometry of the inactivation of thrombin by ATIII is 1:1. The clotting assay for measurement of ATIII is an indirect assay that reflects the loss of thrombin activity. Therefore, the ATIII levels are calculated indirectly by calculating the loss of thrombin activity. From FIG. 23, the ATIII levels can be obtained from the clotting times.

(11)

IMMUNOLOGICAL ASSAY

HEPARIN ASSAYS

The unique features of the heparin assay are that:

(1) the sensitivity and specificity of the PT, TCT, and APTT for heparin at therapeutic ranges; (2) the specificity and sensitivity of heparin assays are not conferred by the heparin source (beef or porcine), or the purity of the thrombin reagent; (3) powdered heparin is more stable than liquid reagents; (4) computerized standard curves for heparin assays can be obtained.

Heparin assays in other laboratories:

(1) The APTT assay is the most widely used. APTT is sensitive to heparin but cannot measure heparin levels in plasma;(2) There is widespread confusion as to the sensitivity of heparin assays using different animal sources and curves are prepared fresh each day.

In the present invention, test sensitivity to heparin was measured for three tests: the PT, APTT, and TCT. Their sensitivity to both liquid and powdered heparin was measured. The experimental condition and procedures were the same for both types of heparin.

Historically, therapeutic heparin ranges were described as the amount of heparin that will prolong the whole blood clotting time to twice baseline value by the Lee and White assay (citation). Later, clinical trials were conducted with heparin on patients with thrombotic disease. It was then determined that plasma levels of 0.2 to 0.4 unit/ml heparin were sufficient to keep the patients anticoagulated. When heparin was administered at higher doses it was found that plasma heparin levels of 0.5 unit/ml or higher resulted in increased bleeding tendency. Heparin plasma levels of 0.2 unit/ml were not adequate to check the thrombotic process.

At the present, the Lee and White clotting time assay is rarely performed. The most widely used laboratory procedure for monitoring heparin therapy is the APTT. The TCT is considered by some to be a more reliable test. However, there are no reports on the use of the PT assay for monitoring heparin.

Powdered heparin:

2 mg of 162 units/mg powdered heparin (sodium), obtained through Sigma Chemical Co., St. Louis, Mo., was added to 32.4 ml of distilled water. This stock solution was reconstituted form each test to a concentration of 0.1 unit/ ml.

Liquid heparin:

10 ul of liquid heparin (sodium), obtained through Elkins-Sinn, Inc., Cherry Hill, N.J., was added to 10 ml of distilled water. This solution was then reconstituted to a concentration of 0.1 u/ml.

Test Procedures:

All tests were performed on Helena Laboratory's Dataclot-2™ fibrometer using pooled normal plasma obtained from 40 healthy donors age 18 to 64 stored at a temperature of −70° C. All plasma and reagents were transferred using MLA pipettes.

Thromboplastin-C (Rabbit brain) obtained from American Dade AHS del Caribe, Inc., Aguada, Puerto Rico, 00602, was used as the reagent for the PT tests.

For the TCT test, thrombin was prepared to give an activity of 1.2 NIH unit.

The PT and TCT were performed 10 times on pooled normal plasma with no heparin added to obtain baseline clotting times. Then, 10 ul of 0.1 u/ml heparin was added to the plasma and four clotting times were obtained. Then, 20 ul of 0.1 u/ml heparin was added to the plasma and four clotting times were obtained. Each new concentration of heparin was increased by 0.1 u/kml increments in this manner until the clotting times became so long that accurate data collection was no longer possible.

The entire procedure was repeated three times, each time with newly reconstituted heparin and other reagents.

The APTT reagents were comprised of Thrombosil-I (Rabbit brain cephalin and silica activator) Lot 3 1TH111 and Calcium Chloride Solution (0.02M aq.) Lot # CAL 300. Both were obtained from Ortho Diagnostic Systems, Inc., Raritan, N.J. 08869.

The APTT test was performed in the same manner with the exception that the initial heparin concentration was 0.05 u/ml and each new heparin concentration value was increased by 0.05 u/ml, rather than by 0.1 u/ml as in the PT and TCT test procedures.

A representative graph is shown in FIG. 23. FIG. 14 shows the chart for recording antithrombin III.

(12) Protein C

Protein C is the zymogen of a serine protease, Protein $C_A$. Protein $C_A$ exerts an anticoagulant effect in plasma by the selective inactivation of non-enzymic activated cofactors FVa and FVIIIa. It has been shown by several investigators that native Factors V and VIII are poor substrates for Protein $C_A$. It has also been shown that on endothelial cell surfaces in blood, Protein C is activated to a protease by thrombin complexed with thrombomodulin. Thrombomodulin is an integral endothelial cell surface protein.

In vitro Protein C is slowly activated by thrombin alone or by thrombin/thrombomodulin at a much faster rate. Also Protein C is activated by purified Factor $X_a$ and by Akistrodon Akistrodon Contortrix venom of the Southern Copperhead snake. The component in the Akistrodon venom that is selective for the activation of Protein C has been purified and is given the trade name "PROTAC"® (available from Sigma Chemical Company, St. Louis, Mo.). In addition to activating Protein C, the purified component of Akistrodon Akistrodon Contortrix has been found to decrease, by direct proteolysis, the procoagulant activities of purified Factors II, VII, IX, X, and to cleave the A alpha chain of fibrinogen (Thrombomodulin Activityin Commercial Thromboplastin Preparations. Thrombos Res. 43, 265–274 (1986)). Thus, in vitro, the Protein C activator from the Southern Copperhead snake venom exerts a broad substrate specificity.

Several assays to measure the biological activity of Protein C in plasma have been published. Some utilize lengthy and rather complicated experimental procedures that preclude their use in clinical diagnostic laboratories. Others use the purified Protein C activator from Akistrodon venom to measure Protein C activity as a function of the prologation of the APTT clotting times.

A. Principle of the Protein C Assay

Plasma is activated by thrombomodulin/tissue Factor and calcium chloride.

Amount of tissue Factor and calcium chloride that activate plasma was carefully calculated. As little as 20 ul of commercial ThromboplAstin/CaCl$_2$ 0.02M solution activates PNP. Evidence for generation of thrombin in the activated plasma is obtained by an increase in Factor V and Factor VIII activity without detectable fibrin formation.

The maximum amount of Thromboplastin/CaCl$_2$ 0.02M solution that fully activates PNP without detectable fibrin formation is 50 ul.

To prepare a suitable commercial Thromboplastin/CaCl$_2$ 0.02M solution that will activate plasma at the recommended 20 ul to 50 ul range, distilled water is added to the dried powder to give in a fibrometer a clotting time by the PT assay for PNP of 11.6 seconds (0.5). The reagent recommended is Ortho Thromboplastin for its high thrombomodulin activity.

Measurement of Activated Factors V and VII by the APTT assay.

30 ul plasma before activation and 30 ul plasma after activation are each added to 70 ul Factor V and Factor VIII deficient plasma. Measurement of change in activity is a change in the clotting time by the APTT assay. Activity is derived from the standard curves presented in the Table shown in FIG. 29. The Table of FIG. 29 shows standard curves for descending ranges of Factors V, VIII, IX, X and XI activities and the mean clotting times obtained by the APTT assay. A least squares linear regression of the actual data points from the straight lines of the best fit are shown in FIG. 29. Factor activities and the corresponding clotting that represent the critical threshold procoagulant Factor V, VIII, IX, X or XI activities are shown.

Protein C is activated in Activated Plasma by Akistrodon Contortrix

Protein C in Activated Plasma is activated by 80 to 100 ng Akistrodon Akistrodon Contortrix (Southern Copperhead Venom). The proteolytic activity of snake venom used, 80 to 100 ng, is selective for Protein C.

The activation of Protein C with Akistrodon is used to speed the process that is started by thrombin/thrombomodulin CaCl$_2$ as described above. If the snake venom step is omitted, a time interval of at least 4 hours is necessary for the inactivation of Factors V$_a$ and Factors VIII$_a$ by "thrombin activated Protein Ca".

B. Biological Activity of Protein C$_A$ is measured as a function of percent change in Factor V and Factor VIII activity.

At the end of one hour incubation, 30 ul of plasma mixture are added to 70 ul of Factor V and Factor VIII deficient plasma. Factor activity is obtained from clotting times by means of standard curves in FIG. 29.

MATERIALS AND REAGENTS

Preparation of Pooled Normal Plasma (PNP)

Human pooled normal plasma (PNP) was prepared from forty healthy blood donors ages 18 to 64 years. Blood (4.5 ml) was drawn from each donor into vacutainer tubes each containing 0.5 ml of 3.85% acidified sodium citrate solution. Blood was spun at 2,000 r.p.m. in a refrigerated Beckman table top centrifuge at 2° C. for 10 to 15 minutes. Platelet poor plasma was pooled into a polystyrene beaker placed on ice. The pooled plasma was assayed for procoagulant factor levels by the PT and APTT assays. Fibrinogen levels were determined by clotting and chemical assays. PNP aliquots (1 ml) were pipetted into 4 ml polystyrene capped tubes and stored at −80° C. for use in the Protein C experiments.

Akistrodon Contortrix Venom (Southern Copperhead venom)

One gram freeze dried venom powder was purchased from Sigma Chemical Company, St. Louis, Mo. Twenty samples of dried powder were weighed 0.1 mg each and stored in 15 ml graduated capped plastic centrifuge tubes at 4° C. until further use. The dried venom was dissolved in distilled water (0.1 mg/10 ml) and assayed for stability by adding 500 ng/50 ul to 1 ml PNP. The proteolytic anticoagulant activity was tested by the APTT assay. Proteolytic anticoagulant activity was markedly decreased within 24 hours after reconstitution in distilled water. Proteolytic anticoagulant activity was retained in the dried powder. Fresh solutions therefore were prepared daily by adding 10 ml distilled water to the graduated plastic centrifuge tubes containing 0.1 mg of dried powder. Venom solutions were kept on ice for the duration of the experiments.

The venom was also tested at two concentrations of 80 ng and 500 ng added to 1 ml PNP for substrate selectivity by PT, APTT and thrombin Clotting Time (TCT) assays.

Tissue Thromboplastin/Calcium Chloride Powder (TTP/CaCl$_2$)

This was purchased from Ortho Diagnostic Systems Inc., Raritan, N.J. Ortho Brain thromboplastin ISI Standard lot 871007 was obtained from the same source. The commercially prepared tissue thromboplastin/calcium chloride powder was reconstituted to give a clotting time of 11.6±0.5 seconds on 100 ul PNP. This reagent has high thrombomodulin activity (Thrombomodulin Activity in Commercial Thromboplastin Preparations. Thrombos Res. 43, 265–274 (1986)).

Activated Partial Thromboplastin Reagent

Thrombosil I, a commercially prepared brain cephalin with silica activator, was purchased from Ortho Diagnostic Systems.

Calcium Chloride Reagent 0.02 molar solution and Thrombofax Reagent. A bovine brain cephalin solution were also purchased from Ortho Diagnostic Systems.

Human Alpha Thrombin with a specific activity of 3,000 units/ug was prepared. Clotting activity of the thrombin in 0.1M CaCl$_2$ solutions is retained for several years. A preservative, Thimerosal purchased from Sigma Chemical Company is added to the thrombin solutions at 1/100,000 (weight in mg/volume). Thrombin solutions (1.5 to 1.2 unit per 100 ul 0.1M CaCl$_2$) were prepared to give a clotting time of 8–10 seconds with 200 ul PNP.

Equipment

A Dataclot 2 fibrometer, Helena Laboratories, Beaumont, Tex. was used for the clotting experiments. A Macintosh Apple Computer and an IBM PC were used for the analysis and graphing of the data.

EXPERIMENTAL PROCEDURES

Prothrombin Time (PT) Assay

PNP or plasma mixture (100 ul) were clotted with 200 ul TTP/CaCl$_2$ solution. The clotting times were recorded on a fibrometer.

Activated Partial Thromboplastin Time (APTT) Assay

PNP or plasma mixture (100 ul) were incubated with APTT reagent for 3 to 5 minutes then clotted with 100 ul CaCl$_2$ 0.02 M.

Thrombin Clotting Time (TCT) Assay 200 ul PNP or plasma mixture was clotted with 100 ul thrombin solution (1.5 to 1.2 unit).

Single Factor Genetically Deficient Plasma Reagents (less than 1% activity)

Factor XI deficient reagent was purchased from George King, Biomedical, Inc., Overland Park, Kans. All other factor deficient plasmas were obtained by plasmapherisis from patients at Michigan State University, East Lansing, Mich.

Standard Curves for Factors V, VII, VIII, IX, X, XI were constructed using single factor genetically deficient plasma and PNP. The clotting times by PT and APTT assays for about forty estimates per point were analyzed. Standard deviation, linear regression, Pearson's correlation coefficient, as well as mean and median were calculated for each curve.

In FIG. 28 the clotting times by PT for Factors V, VII and X activities ranging from 80% to less than 1% are presented.

In FIG. 29 the data presented are the clotting times by the APTT assay for Factors V, VIII, IX, X, and XI activities ranging from 80% to less than 1%.

Factor Assays:

In the Protein C assay experiments, most of the Factor assays were performed by PT or APTT assay after adding 30 ul plasma mixtures to 70 ul single factor deficient plasma (Factors V, VII, VIII, IX, X, XI or XII) and recording the mean clotting times. The mean clotting time was never less than four estimates with an average of ten estimates per point. Factor activities were then derived from the corresponding clotting times on the linear regression of the standard curves.

Activation of Plasma

One milliliter of PNP or patient plasma was activated by adding 50 ul, 30 ul, 20 ul or 10 ul solutions of TTP/CaCl$_2$. Tube was gently shaken and incubated at 37° C. for times ranging from zero to one hour. PT, APTT, TCT, and Factor assays were performed on activated plasma and on plasma prior to activation.

Standard Curves for Protein C

Three standard curves for Protein C were contructed in:

1) Protein C freeze dried deficient plasma reagent purchased from Diagnostica Stago, Asniere, France.

2) Plasma obtained froma 16 year-old patient who tried to commit suicide by ingestion of three packages of a long lasting coumarin derivative prepared commercially and used as a rat poison (trade name: Enforcer™). PT was 72 secs (control 11.2 secs), APTT 132.4 secs (control 26.4 secs), and TCT 9.9 secs (control 9.2 secs). Factor VII activity in this patient's plasma was less than 1%, Factor X activity 2%, and FIX activity 2.5%.

3) PNP immunodepleted of Protein C by anti-Protein C insolubilized rabbit immunoglobulins.

Human anti Protein C antibodies were purchased from Diagnostica Stago Asniere, France. The commercial antibodies were not charcterized in my laboratory for antigen specificity and cross-reactivity. Coupling of the anti Protein C antibodies to sepharose beads and immuno depletion of PNP by insolubilized antibodies was performed exactly as described (H. I. Hassouna and J. A. Penner. Sem. Thromb. Haemost. Vol. 7, No. 2, pp. 61–111 (1981)).

Patient Tests

Following surgery for cancer of the pancreas, a 61 year old patient suffered a pulmonary embolism. He was placed on coumadin, 5 mg/day. Two months later, while still on coumadin, he was hospitalized for spontaneous bleeding, bruising and a hematoma on the left thigh. He had lost eight pounds because he was not eating.

At the time of admission, his PT was 60 seconds, APTT greater than 100 seconds, platelet count 140,000/cc, fibrinogen 425 mg/dl, and fibrin split products moderately elevated. Liver function tests were unchanged from previous records.

He was diagnosed as disseminated intravascular coagulation (DIC), was taken off coumadin and given fresh frozen plasma. His PT and APTT corrected for six hours. For the next three days, his PT and APTT were still prolonged; PT 20–22 seconds (control 11.6 secs.) and his APTT 38 seconds (control 26.4 secs.). Fibrinogen remained unchanged, at 425 mg/dl. Fibrin split products were not ordered.

Discussion

The diagnosis of DIC was made on the basis of a prolonged PT and APTT and a mild elevation of fibrin split products. The fact that fibrinogen levels and platelet counts were within normal range was attributed to a possible decline in initially higher than normal values. Other possible diagnoses were disregarded, owing to the myth that an APTT is never prolonged with coumadin therapy and that a PT of 60 seconds is possible even with fibrinogen levels of 425 mg/dl. Also the specificity of immunoassays for the determination of fibrin split products was never questioned.

In this case, access to the present invention data would have given the clinician the ability to make the correct diagnosis.

1) The Prothrombin Time (PT) test measures Factor VII, as well as Fibrinogen, Factors V, X, and prothrombin. This can be seen in FIG. 1 (Coagulation Screening Tests). Also, maximal prolongation of the clotting times by the PT test for a single factor deficiency is less than 50 seconds, provided fibrinogen levels are normal (see FIG. 2 top section and FIG. 3). Similarly, maximal prolongation of the clotting times by the Activated Partial Thromboplastin Time (APTT) test for Factor VIII deficiency is 77–80 seconds (see FIG. 2—lower section and FIG. 5). Drugs, such as coumadin, that interfere with the synthesis of biologically active vitamin K dependent factors have an effect on the PT as well as the APTT (see FIG. 5—4th section from bottom of page). PT or APTT tests are considered prolonged if the clotting times are outside the normal distribution. Normal distributions for both the PT and APTT are indicated in the top section of Table V and detailed in the histograms marked FIGS. 6 and 7. In DIC, Factors V and VIII are the major procoagulant factors consumed. The half lives of Factors V and VIII are 12–36 hours and 2.9 days respectively (see FIG. 8).

2) When the patient was given fresh frozen plasma, the PT and APTT corrected for six hours then became prolonged again. The prolonged coagulation times, though modest, were significant.

3) We can therefore contemplate one of two conditions:

a) a low grade ongoing disseminated intravascular coagulation or (b) a multiple deficiency involving the vitamin K dependent factors due to malnutrition and possible malabsorption associated with coumadin therapy.

4) Confirmatory tests are indicated in table IX (Diagnosis of Acute Thrombosis). Testing for Antithrombin III, Protein C, and plasminogen will provide proof for or refute DIC.

Another approach would be to test for Factor V. If Factor V levels are within the normal range, a diagnosis for vitamin K deficiency can be made.

Diagnosis

Vitamin K deficiency due to malnutrition and possible malabsorption associated with coumadin therapy.

Better diagnostic tests for diseases caused by abnormal blood clot formation (heart disease, strokes, deep clots in lungs, legs) are in demand. These conditions are an enormous health problem and public awareness of them has been increasing steadily with growth in health consciousness. They are life threatening diseases associated with aging, lack of exercise, poor dietary habits, smoking and oral contraception so they have a lot of visibility. Thrombotic (clotting) disorders are being handled now with new treatments, like tPA and oral anticoagulants, that complicate the interpretation of laboratory tests needed for diagnosis and for monitoring therapy.

There is already an established market for coagulation disease diagnostic kit sales to the medical-technology community. The fact is though that this traditional technology, based on concepts prevalent in the 1950's, does not provide the quantitative precision that is essential for this expanding market and for the complexities that result from modern medical and surgical management of coagulation diseases. The present invention is a validated, proven system of original assays, founded on a very extensive data-base of thousands of test results on samples from diseased and normal subjects. It is compiled in a comprehensive, differential-diagnostic format and relies on some preferred reagents with highly desirable characteristics. The system makes high quality information available to the diagnostician conveniently and quickly, improving the decision-making process for the clinician. It can even identify those "at risk" of clot formation and therefore has the potential for incorporation into screening panels for routine use.

The preceding description is only illustrative of the present invention and it is intended that the present invention be limited only to the hereinafter appended claims.

I claim:

1. In a method for diagnosing blood clotting disorders in humans by:

(a) separately standardizing activated partial thromboplastin (APT), prothrombin reagents (P) and thrombin (T) to produce a particular predetermined standardized clotting time with pooled normal plasma (PNP);

(b) separately testing sets of a sample of plasma separated from the blood of a patient and sets of a sample of plasma from PNP from healthy humans for clotting time by addition of predetermined amounts of P to a first set of the sample; APT to a second set of each sample and T to a third set of each sample;

(c) optionally testing each sample for hypercoagulation or bleeding based upon the P, APT and T tests and charting the results so that the sample plasma and PNP tests can be compared with each other; and (d) making a diagnosis based upon the differences of clotting time based upon the tests, the improvement which consists essentially of: testing a fourth set of the sample of the plasma from the patient and the sample of the plasma from PNP separately for bleeding by mixing a volume of a genetic factor deficient plasma (GFDP) with PNP in an amount between about 40 and 60 percent by volume of GPDP to PNP and separately with patient plasma so that there is activity with the 40 to 60 percent by the volume GFDP which is equivalent inactivity to eighty percent by volume of the GFDP, wherein the GFDP is known to be genetically deficient in a blood factor selected from the group consisting of Factors V, VII, VIII, IX, X, XI, XII, F1.F and high molecular weight kininogen, the PNP mixed with the 40 to 60% GFDP produces a standardized clotting time when coagulated with an appropriate one of P or APT or both separately and the clotting time is determined for the mixture, the results for the clotting time are charted on a side-by-side basis for the patient and the PNP, the results are compared with a factor data base showing a normal range for each factor based upon the PNP and wherein the clotting time of GFDP is corrected by the PNP and by patient plasma which contains an amount of the factor which is normal.

2. The method of claim 1 wherein in addition the sample of the plasma from the patient is tested for antithrombin III (ATIII) and the results are compared with an antithrombin III data base showing normal ranges of clotting time.

3. The method of claim 1 wherein in addition the samples of plasma from the patient and the PNP are tested for protein C in activated form using P or APT and genetic factor deficient plasma (GFDP) deficient in Factor V or Factor VIII, wherein the results for the patient and the PNP are charted on a side-by-side basis, wherein the results are compared with a protein C data base showing normal ranges based upon the PNP and wherein normal patient plasma inhibits activated Factors V and VIII to produce a prolonged clotting time.

4. The method of claim 1 wherein in addition the samples of the plasma of the patient and the PNP are tested for fibrinogen by determining clotting time using T and multiple dilutions of the plasma with defibrillated PNP, wherein the results for the patient and the PNP are charted on a side-by-side basis and wherein the results are compared with a fibrinogen data base showing normal ranges based upon the PNP.

5. The method of claim 1 wherein the data base is maintained in a computer.

6. The method of claim 1 wherein the charts are maintained as screens on a computer which can be completed for each patient and optionally printed out on a printer connected to the computer.

7. The method of claim 1 wherein the data base is maintained in a computer and wherein the charts are maintained as screens on the computer which are completed for each patient as the tests are performed.

8. The method of claim 1 wherein a computer program provides a basis for differential diagnosis based upon the clotting time for P, APT and T and suggests further tests for hyperclotting or excess bleeding.

9. The method of claim 1 wherein in addition the sample of the plasma from the patient is tested for antithrombin III (ATIII) and the results compared with an antithrombin III data base showing normal and abnormal ranges;

wherein in addition the samples of plasma from the patient and the PNP are tested for protein C in activated form using P or APT and GFDP deficient in Factor V or in Factor VIII, wherein the results for the patient and the PNP are charted on a side-by-side basis, wherein the results are compared with a protein C data base showing normal ranges based upon the PNP and wherein normal patient plasma inhibits activated Factors V and VIII to produce a prolonged clotting time; and wherein in addition samples of the plasma of the patient and the PNP are tested for fibrinogen by determining clotting time using T and multiple dilutions of the plasma with defibrillated PNP, wherein the results for the patient and the PNP are charted on a side-by-side basis and wherein the results are compared with a fibrinogen data base showing normal ranges based upon the PNP.

10. The method of claim 9 wherein the results are combined on a single chart for bleeding disorders or for hypercoagulation.

11. The method of claim 9 wherein the data bases are provided on a program in a computer.

12. The method of claim 11 wherein the charts are maintained as screens on the computer which are completed as the tests are performed.

13. The method of claim 12 wherein the computer integrates the test results from the data bases to provide a suggested diagnosis.

14. A method for diagnosing blood clotting disorders in humans which consists essentially of:

(a) separately standardizing activated partial thromboplastin (APT), prothrombin reagents (P) and thrombin (T) to produce a particular predetermined standardized clotting time with pooled normal plasma (PNP);

(b) separately testing samples of plasma from a patient and pooled plasma from PNP for the times to coagulate by P, APT and T;

(c) testing the of the plasma from the patient and PNP by mixing a blood sample known to be genetically deficient in a blood factor selected from the group consisting of Factors V, VII, VIII, IX, X, XI, XII, F1.F and high molecular weight kininogen with a volume of a genetic factor deficient plasma GFDP in an amount between about 40 to 60 percent of GFDP to PNP and separately between about 40 to 60 percent of the GFDP to patient plasma, wherein the PNP produces a standardized clotting time with the mixture with the 40 to 60 percent by volume of the GFDP when coagulated by an appropriate one of P, APT or both separately, wherein activities of each of the mixtures for the factors are equivalent in activity to eighty percent by volume of the GFDP, charting the results together on a side-by-side basis and comparing the results with a second data base showing abnormal and normal ranges of clotting time based upon PNP and wherein the clotting time of GFDP is corrected by the PNP and patient plasma which contains an amount of the factor which is normal;

(d) testing the samples of the plasma from the patient and PNP for anti-thrombin III by determining the clotting time for the patient and PNP, charting the results together on a side-by-side basis and comparing the results with an antithrombin III data base showing normal ranges for PNP;

(e) testing the samples of the plasma for protein C by determining the clotting time and charting the results and comparing the results with a protein C data base showing normal ranges of clotting time based upon the PNP;

(f) testing the samples of plasma for fibrinogen from the patient plasma and PNP and determining clotting time for coagulation by T at known dilutions of the plasma with defibrillated PNP, charting the results as the clotting time on a side-by-side basis and comparing the results with a fibrinogen data base showing normal ranges of the clotting time for the PNP; and (g) making a diagnosis of a blood clotting disorder based upon the differences in the clotting times in the tests.

15. The method of claim 14 wherein the data bases are in a program in a computer.

* * * * *